United States Patent
Caligiuri et al.

(10) Patent No.: US 10,775,387 B2
(45) Date of Patent: Sep. 15, 2020

(54) DETECTION OF PLATELET-DERIVED SHED CD31

(71) Applicants: Institut National de la Sante et de la Recherche Medicale (INSERM), Paris (FR); Universite Paris Diderot—Paris 7, Paris (FR); Universite Paris 13—Paris Nord, Villetaneuse (FR); Assistance Publique—Hopitaux de Paris, Paris (FR)

(72) Inventors: Giuseppina Caligiuri, Paris (FR); Antonino Nicoletti, Paris (FR)

(73) Assignees: INSTITUT NATIONAL DE LA SANTE ET DE LA RECHERCHE MEDICALE (INSERM), Paris (FR); UNIVERSITE DE PARIS, Paris (FR); UNIVERSITE PARIS 13—PARIS NORD, Villetaneuse (FR); ASSISTANCE PUBLIQUE—HOPITAUX DE PARIS, Paris (FR)

(*) Notice: Subject to any disclaimer, the term of this patent is extended or adjusted under 35 U.S.C. 154(b) by 218 days.

(21) Appl. No.: 15/358,213

(22) Filed: Nov. 22, 2016

(65) Prior Publication Data
US 2017/0067910 A1 Mar. 9, 2017

Related U.S. Application Data

(62) Division of application No. 14/391,849, filed as application No. PCT/EP2013/055489 on Mar. 15, 2013, now Pat. No. 9,534,036.

(60) Provisional application No. 61/622,672, filed on Apr. 11, 2012.

(30) Foreign Application Priority Data

Apr. 11, 2012 (EP) .................. 12305429

(51) Int. Cl.
- *G01N 33/68* (2006.01)
- *G01N 33/543* (2006.01)
- *G01N 33/86* (2006.01)
- *C07K 14/705* (2006.01)

(52) U.S. Cl.
CPC ... *G01N 33/6872* (2013.01); *C07K 14/70503* (2013.01); *G01N 33/54313* (2013.01); *G01N 33/6893* (2013.01); *G01N 33/86* (2013.01); *G01N 2333/70503* (2013.01); *G01N 2800/226* (2013.01); *G01N 2800/24* (2013.01); *G01N 2800/52* (2013.01)

(58) Field of Classification Search
None
See application file for complete search history.

(56) References Cited

FOREIGN PATENT DOCUMENTS

WO 2010000756 1/2010

OTHER PUBLICATIONS

Danese et al., "Platelets in inflammatory bowel disease: clinical, pathogenic, and therapeutic implications", Am J Gastroenterol. May 2004;99(5):938-45.
Fawcett et al., "Mapping the homotypic binding sites in CD31 and the role of CD31 adhesion in the formation of interendothelial cell contacts", J Cell Biol. Mar. 1995;128(6):1229-41.
Fornasa et al. "A CD31-derived peptide prevents angiotensin II-induced atherosclerosis progression and aneurysm formation", Cardiovasc Res. Apr. 1, 2012;94(1):30-7.
Fornasa et al., "TCR stimulation drives cleavage and shedding of the ITIM receptor CD31", J Immunol. May 15, 2010;184(10):5485-92.
Goldberger et al., "Biosynthesis and processing of the cell adhesion molecule PECAM-1 includes production of a soluble form", J Biol Chem. Jun. 24, 1994;269(25):17183-91.
Prevost et al., "Granulocyte-macrophage colony-stimulating factor (GM-CSF) and inflammatory stimuli up-regulate secretion of the soluble GM-CSF receptor in human monocytes: evidence for ectodomain shedding of the cell surface GM-CSF receptor alpha", subunit, J Immunol. Nov. 15, 2002;169(10):5679-8.
Sheremata et al., "Evidence of platelet activation in multiple sclerosis", J Neuroinflammation. Jun. 27, 2008;5:27.
Yan et al., "Localization of multiple functional domains on human PECAM-1 (CD31) by monoclonal antibody epitope mapping", Cell Adhes Commun. Feb. 1995;3(1):45-66.
Zimmerman et al., "Immunology. Arsonists in rheumatoid arthritis", Science. Jan. 29, 2010;327(5965):528-9.
International search report of application PCT/EP2013/055489.

*Primary Examiner* — James H Alstrum-Acevedo
*Assistant Examiner* — Tara L Martinez
(74) *Attorney, Agent, or Firm* — W&C IP

(57) ABSTRACT

The present invention relates to various soluble forms of CD31, including a novel form which is shed by activated platelets and released into the circulation. Methods for detecting said soluble forms of CD31 are disclosed, as are methods of specifically 1 detecting said platelet-derived shed CD31 and the use of such methods as a diagnostic tool.

15 Claims, 4 Drawing Sheets

Specification includes a Sequence Listing.

FIG.2

SEQUENCE LISTING

```
<160> NUMBER OF SEQ ID NOS: 1

<210> SEQ ID NO 1
<211> LENGTH: 738
<212> TYPE: PRT
<213> ORGANISM: Homo sapiens
<220> FEATURE:
<221> NAME/KEY: SIGNAL
<222> LOCATION: (1)..(27)
<220> FEATURE:
<221> NAME/KEY: DOMAIN
<222> LOCATION: (28)..(601)
<223> OTHER INFORMATION: extracellular domain
<220> FEATURE:
<221> NAME/KEY: DOMAIN
<222> LOCATION: (34)..(121)
<223> OTHER INFORMATION: First Ig-like domain
<220> FEATURE:
<221> NAME/KEY: DOMAIN
<222> LOCATION: (145)..(233)
<223> OTHER INFORMATION: Second Ig-like domain
<220> FEATURE:
<221> NAME/KEY: DOMAIN
<222> LOCATION: (236)..(315)
<223> OTHER INFORMATION: Third Ig-like domain
<220> FEATURE:
<221> NAME/KEY: DOMAIN
<222> LOCATION: (328)..(401)
<223> OTHER INFORMATION: Fourth Ig-like domain
<220> FEATURE:
<221> NAME/KEY: DOMAIN
<222> LOCATION: (424)..(493)
<223> OTHER INFORMATION: Fifth Ig-like domain
<220> FEATURE:
<221> NAME/KEY: DOMAIN
<222> LOCATION: (499)..(591)
<223> OTHER INFORMATION: Sixth Ig-like domain
<220> FEATURE:
<221> NAME/KEY: DOMAIN
<222> LOCATION: (592)..(601)
<223> OTHER INFORMATION: Juxta-membrane domain
<220> FEATURE:
<221> NAME/KEY: DOMAIN
<222> LOCATION: (602)..(620)
<223> OTHER INFORMATION: transmembrane domain
<220> FEATURE:
```

```
<221> NAME/KEY: DOMAIN
<222> LOCATION: (621)..(738)
<223> OTHER INFORMATION: cytoplasmic

<400> SEQUENCE: 1
```

| | | | | | | | | | | | | | | |
|---|---|---|---|---|---|---|---|---|---|---|---|---|---|---|
| Met | Gln | Pro | Arg | Trp | Ala | Gln | Gly | Ala | Thr | Met | Trp | Leu | Val | Leu |
| 1 | | | | 5 | | | | | 10 | | | | | 15 |
| Leu | Thr | Leu | Leu | Leu | Cys | Ser | Ser | Leu | Glu | Gly | Gln | Glu | Asn | Ser | Phe |
| | | | 20 | | | | | 25 | | | | | 30 | | |
| Thr | Ile | Asn | Ser | Val | Asp | Met | Lys | Ser | Leu | Pro | Asp | Trp | Thr | Val | Gln |
| | | 35 | | | | | 40 | | | | | 45 | | | |
| Asn | Gly | Lys | Asn | Leu | Thr | Leu | Gln | Cys | Phe | Ala | Asp | Val | Ser | Thr | Thr |
| | 50 | | | | | 55 | | | | | 60 | | | | |
| Ser | His | Val | Lys | Pro | Gln | His | Gln | Met | Leu | Phe | Tyr | Lys | Asp | Asp | Val |
| 65 | | | | | 70 | | | | | 75 | | | | | 80 |
| Leu | Phe | Tyr | Asn | Ile | Ser | Ser | Met | Lys | Ser | Thr | Glu | Ser | Tyr | Phe | Ile |
| | | | | 85 | | | | | 90 | | | | | 95 | |
| Pro | Glu | Val | Arg | Ile | Tyr | Asp | Ser | Gly | Thr | Tyr | Lys | Cys | Thr | Val | Ile |
| | | | 100 | | | | | 105 | | | | | 110 | | |
| Val | Asn | Asn | Lys | Glu | Lys | Thr | Thr | Ala | Glu | Tyr | Gln | Leu | Leu | Val | Glu |
| | | 115 | | | | | 120 | | | | | 125 | | | |
| Gly | Val | Pro | Ser | Pro | Arg | Val | Thr | Leu | Asp | Lys | Lys | Glu | Ala | Ile | Gln |
| | 130 | | | | | 135 | | | | | 140 | | | | |
| Gly | Gly | Ile | Val | Arg | Val | Asn | Cys | Ser | Val | Pro | Glu | Glu | Lys | Ala | Pro |
| 145 | | | | | 150 | | | | | 155 | | | | | 160 |
| Ile | His | Phe | Thr | Ile | Glu | Lys | Leu | Glu | Leu | Asn | Glu | Lys | Met | Val | Lys |
| | | | | 165 | | | | | 170 | | | | | 175 | |
| Leu | Lys | Arg | Glu | Lys | Asn | Ser | Arg | Asp | Gln | Asn | Phe | Val | Ile | Leu | Glu |
| | | | 180 | | | | | 185 | | | | | 190 | | |
| Phe | Pro | Val | Glu | Glu | Gln | Asp | Arg | Val | Leu | Ser | Phe | Arg | Cys | Gln | Ala |
| | | | 195 | | | | | 200 | | | | | 205 | | |
| Arg | Ile | Ile | Ser | Gly | Ile | His | Met | Gln | Thr | Ser | Glu | Ser | Thr | Lys | Ser |
| | | 210 | | | | | 215 | | | | | 220 | | | |
| Glu | Leu | Val | Thr | Val | Thr | Glu | Ser | Phe | Ser | Thr | Pro | Lys | Phe | His | Ile |
| 225 | | | | | 230 | | | | | 235 | | | | | 240 |
| Ser | Pro | Thr | Gly | Met | Ile | Met | Glu | Gly | Ala | Gln | Leu | His | Ile | Lys | Cys |
| | | | | 245 | | | | | 250 | | | | | 255 | |
| Thr | Ile | Gln | Val | Thr | His | Leu | Ala | Gln | Glu | Phe | Pro | Glu | Ile | Ile | Ile |
| | | | 260 | | | | | 265 | | | | | 270 | | |
| Gln | Lys | Asp | Lys | Ala | Ile | Val | Ala | His | Asn | Arg | His | Gly | Asn | Lys | Ala |
| | | 275 | | | | | 280 | | | | | 285 | | | |
| Val | Tyr | Ser | Val | Met | Ala | Met | Val | Glu | His | Ser | Gly | Asn | Tyr | Thr | Cys |
| | 290 | | | | | 295 | | | | | 300 | | | | |
| Lys | Val | Glu | Ser | Ser | Arg | Ile | Ser | Lys | Val | Ser | Ser | Ile | Val | Val | Asn |
| 305 | | | | | 310 | | | | | 315 | | | | | 320 |
| Ile | Thr | Glu | Leu | Phe | Ser | Lys | Pro | Glu | Leu | Gly | Ser | Ser | Phe | Thr | His |
| | | | | 325 | | | | | 330 | | | | | 335 | |
| Leu | Asp | Gln | Gly | Glu | Arg | Leu | Asn | Leu | Ser | Cys | Ser | Ile | Pro | Gly | Ala |
| | | | 340 | | | | | 345 | | | | | 350 | | |
| Pro | Pro | Ala | Asn | Phe | Thr | Ile | Gln | Lys | Glu | Asp | Thr | Ile | Val | Ser | Gln |
| | | 355 | | | | | 360 | | | | | 365 | | | |
| Thr | Gln | Asp | Phe | Thr | Lys | Ile | Ala | Ser | Lys | Ser | Asp | Ser | Gly | Thr | Tyr |
| | 370 | | | | | 375 | | | | | 380 | | | | |
| Ile | Cys | Thr | Ala | Gly | Ile | Asp | Lys | Val | Val | Lys | Lys | Ser | Asn | Thr | Val |

```
385                 390                 395                 400
Gln Ile Val Val Cys Glu Met Leu Ser Gln Pro Arg Ile Ser Tyr Asp
                405                 410                 415
Ala Gln Phe Glu Val Ile Lys Gly Gln Thr Ile Glu Val Arg Cys Glu
                420                 425                 430
Ser Ile Ser Gly Thr Leu Pro Ile Ser Tyr Gln Leu Leu Lys Thr Ser
                435                 440                 445
Lys Val Leu Glu Asn Ser Thr Lys Asn Ser Asn Asp Pro Ala Val Phe
    450                 455                 460
Lys Asp Asn Pro Thr Glu Asp Val Glu Tyr Gln Cys Val Ala Asp Asn
465                 470                 475                 480
Cys His Ser His Ala Lys Met Leu Ser Glu Val Leu Arg Val Lys Val
                485                 490                 495
Ile Ala Pro Val Asp Glu Val Gln Ile Ser Ile Leu Ser Ser Lys Val
                500                 505                 510
Val Glu Ser Gly Glu Asp Ile Val Leu Gln Cys Ala Val Asn Glu Gly
                515                 520                 525
Ser Gly Pro Ile Thr Tyr Lys Phe Tyr Arg Glu Lys Glu Gly Lys Pro
    530                 535                 540
Phe Tyr Gln Met Thr Ser Asn Ala Thr Gln Ala Phe Trp Thr Lys Gln
545                 550                 555                 560
Lys Ala Ser Lys Glu Gln Glu Gly Glu Tyr Tyr Cys Thr Ala Phe Asn
                565                 570                 575
Arg Ala Asn His Ala Ser Ser Val Pro Arg Ser Lys Ile Leu Thr Val
                580                 585                 590
Arg Val Ile Leu Ala Pro Trp Lys Lys Gly Leu Ile Ala Val Val Ile
                595                 600                 605
Ile Gly Val Ile Ile Ala Leu Leu Ile Ile Ala Ala Lys Cys Tyr Phe
    610                 615                 620
Leu Arg Lys Ala Lys Ala Lys Gln Met Pro Val Glu Met Ser Arg Pro
625                 630                 635                 640
Ala Val Pro Leu Leu Asn Ser Asn Asn Glu Lys Met Ser Asp Pro Asn
                645                 650                 655
Met Glu Ala Asn Ser His Tyr Gly His Asn Asp Asp Val Arg Asn His
                660                 665                 670
Ala Met Lys Pro Ile Asn Asp Asn Lys Glu Pro Leu Asn Ser Asp Val
                675                 680                 685
Gln Tyr Thr Glu Val Gln Val Ser Ser Ala Glu Ser His Lys Asp Leu
    690                 695                 700
Gly Lys Lys Asp Thr Glu Thr Val Tyr Ser Glu Val Arg Lys Ala Val
705                 710                 715                 720
Pro Asp Ala Val Glu Ser Arg Tyr Ser Arg Thr Glu Gly Ser Leu Asp
                725                 730                 735
Gly Thr
```

DETECTION OF PLATELET-DERIVED SHED CD31

CROSS-REFERENCE TO RELATED APPLICATIONS

This application is a divisional application of U.S. Ser. No. 14/391,849 filed Oct. 10, 2014, now U.S. Pat. No. 9,534,036, which itself was a national stage filing under Rule 371 from PCT/EP2013/055489 filed Mar. 15, 2013, which claimed priority to U.S. Provisional Application 61/622,672 filed Apr. 11, 2012 and priority to European Application 12305429.8 filed Apr. 11, 2012.

FIELD OF THE INVENTION

The present invention relates to various soluble forms of CD31, including a novel form which is shed by activated platelets and released into the circulation. Methods for detecting said soluble forms of CD31 are disclosed, as are methods of specifically detecting said platelet-derived shed CD31 and the use of such methods as a diagnostic tool.

BACKGROUND

CD31, also known as PECAM-1, is a transmembrane inhibitory receptor present on many kinds of haematopoietic cells. It is found on the surface of platelets, monocytes, neutrophils, T and B-cells and endothelial cells.

CD31 is composed of an extracellular domain (ECD) comprising 6 Ig-like domains numbered starting from the most distal from the membrane, a trans-membrane segment and a cytoplasmic tail containing 2 immuno tyrosine-based inhibitory motifs (ITIMs). The latter are not phosphorylated in resting conditions because CD31 does not possess an intrinsic kinase activity.

CD31 molecules on interacting cells bind to each other via a trans-homophilic interaction of the Ig-like domain 1 of the ECD which triggers the clustering of the protein through a cis-homophilic interaction of juxtamembrane sequences of the ECD, thus favouring the phosphorylation of the CD31 intracellular ITIMs by tyrosine kinases carried by other cluster-associated membrane receptors.

Binding of CD31 molecules on interacting cells thus triggers the phosphorylation of intracellular tyrosine inhibitory motifs and the recruitment and activation of SH2-containing phosphatases signalling pathways. Depending on the signalling adaptors associated to the closest membrane receptor, this can lead to either the activation of signalling cascades (e.g. GAB/ERK/MAPK, survival of endothelial cells) or their inhibition (e.g. JAK/STAT, activation of leukocytes and platelets).

The putative immunoregulatory properties of CD31 are supported by the fact that CD31 signaling drives mutual repulsion of blood leukocytes and modulates the balance between inhibitory and stimulatory signals of both innate and adaptive immune cells. A soluble form of CD31 ('splice variant' form of CD31), produced from a variant transcript lacking the transmembrane segment, has been reported to be present in human plasma and is thought to be derived from endothelial cells (Goldberger al al 1994; J Biol Chem 269, 17183-17191). Soluble CD31 comprising the first Ig-like ECD domains can be immunodetected in body fluids by commercially available kits. However, studies attempting to find a correlation between plasma levels of soluble CD31 and the risk of atherothrombosis or other autoimmune diseases gave contradictory results as the data showed a broad range of plasma CD31 values, independently of the specific genetic polymorphisms analyzed.

A part of this puzzle was solved by the inventors' previous identification of an additional soluble form of CD31 derived from a portion of CD31 cleaved and shed by activated lymphocytes, as described in PCT/EP2009/058220 (WO2010/000756). It had long been observed that CD31 is "lost" on certain circulating lymphocytes and upon lymphocyte activation and the assumed absence of lymphocyte CD31 was increased in subjects suffering from atherothrombosis. The inventors found that the assumed loss of CD31 on activated/memory T lymphocytes is actually incomplete and results from the cleavage and shedding of CD31 between the $5^{th}$ and the $6^{th}$ extracellular Ig-like domains. The shed extracellular domain portion of CD31 (referred to as "lymphocyte-derived shed CD31") is released into body fluids and can be detected in the circulation, where it is present together with the soluble splice variant form of CD31. They additionally showed that, after clinical symptoms disappear, high risk of recurrent atherothrombosis is linked with the specific increase of the lymphocyte-derived shed CD31 and the reciprocal decrease of the splice variant CD31 in the circulation. This provided a possible explanation of why immunodetection of the total circulating CD31 (comprising the lymphocyte-derived shed CD31 and the splice variant) by commercially available kits was not of diagnostic value.

This finding created the opportunity to establish diagnostic tools which could distinguish the different forms of soluble CD31. Previous commercially available tests detected plasma CD31 through the use of antibodies directed to CD31 domains 1 to 5, so could not discriminate between the soluble splice variant of CD31 (containing all the 6 extracellular Ig-like domains) and the lymphocyte-derived shed form of CD31 (containing domains 1 to 5 only). The method developed by the inventors and described in WO2010/000756 allowed the simultaneous detection of the $5^{th}$ and of the $6^{th}$ Ig-like domain on soluble CD31 captured from the $1^{st}$ Ig-like domain. This method allowed the lymphocyte-derived shed form (which consists of the first 5 ECD domains and lacks the $6^{th}$ Ig-like domain) to be precisely quantified and distinguished from CD31 forms that comprise the $6^{th}$ Ig-Like domain (such as the described splice variant).

This finding also explained the absence of CD31 signalling on lymphocytes which have shed CD31. CD31 signalling is suppressed by the cleavage and shedding of the first 5 Ig-like domains of the ECD. Due to the loss of the "adhesive" Ig-like domains 1-2, the truncated CD31 cannot be bound by membrane anchored or the soluble splice variant forms of CD31, so CD31 signalling is absent on cells bearing the truncated CD31 molecule. This absence of CD31 signalling favours the activation of leukocytes and leads to pathologies linked to chronic tissue inflammation. The measure of lymphocyte-derived shed CD31 form could therefore reflect the individual risk of inflammatory and thrombotic pathologic processes

DESCRIPTION OF THE INVENTION

The inventors have now identified an additional form of shed CD31 derived from platelets. They have shown that activated platelets cleave extracellular CD31 between the $6^{th}$ extracellular Ig-like domain and the plasma membrane, producing a shed form which can be recognized by antibodies to $6^{th}$ Ig-like domain, unlike the form shed by lymphocytes which lacks the $6^{th}$ Ig-like domain. Upon platelet aggregation, the shed platelet-derived extracellular domain of CD31 (also referred to as "platelet-derived shed ectodomain" or "platelet-derived shed CD31") is released into the circulation, where it is present together with the lymphocyte-derived shed CD31 and the soluble splice variant of CD31.

CD31 is constitutively present also on platelets where it essentially functions as a regulatory molecule. Indeed, in addition to inflammation, defective CD31 signalling also promotes platelet activation and aggregation and thrombosis. The inventors' finding that platelet CD31 also undergoes cleavage and shedding upon platelet activation and aggregation is therefore of significant clinical relevance.

Pathologic platelet activation and aggregation is responsible for acute thrombotic occlusion of small and medium sized arteries, and platelets are a very rich source of inflammatory mediators, thus contributing to the amplification and dissemination of chronic inflammatory diseases such as atherosclerotic diseases and autoimmune conditions. The ability to discriminate between soluble CD31 of lymphocyte, endothelial and platelet origin will thus permit more appropriate treatments for these conditions to be selected in individual patients, thanks to a fuller understanding of the pathologic cellular events underlying the clinical manifestations of a given disease.

The invention therefore provides a fragment of a full-length CD31 protein, said fragment comprising at least a part of the $6^{th}$ Ig-like extracellular domain of said full-length CD31 protein, wherein said fragment does not comprise the intracellular domain of said full-length protein. Said fragment preferably contains at least an epitope within the $6^{th}$ Ig-like domain. Thus, said fragment may be specifically bound by an antibody which specifically binds to an epitope within the $6^{th}$ Ig-like domain. In some embodiments, said fragment does not comprise the juxtamembrane and/or transmembrane domains of said full-length CD31 protein. In some embodiments, said fragment further does not comprise the signal sequence. In preferred embodiments, said fragment comprises or consists of extracellular immunoglobulin-like domains 1 to 6 of said full-length CD31 protein. Preferably, said full-length CD31 protein has at least 80% amino acid sequence identity to the amino acid sequence of SEQ ID No 1.

Thus, the invention provides a fragment as described above, wherein
(i) said $6^{th}$ extracellular immunoglobulin-like domain is or corresponds to amino acids 494-591 of the amino acid sequence of SEQ ID No 1;
(ii) said juxtamembrane domain is or corresponds to amino acids 592-601 of the amino acid sequence of SEQ ID No 1;
(iii) said transmembrane domain is or corresponds to amino acids 602-620 of the amino acid sequence of SEQ ID No 1; and/or
(iv) said intracellular domain is or corresponds to amino acids 621-738 of the amino acid sequence of SEQ ID No 1.

Also provided are isolated proteins comprising or consisting of the CD31 fragments described herein.

All reference to 'comprising' herein should also be understood as including 'consisting of'.

Also provided are methods of detection of platelet aggregation in a subject, said method comprising detection of a platelet-derived shed ectodomain of CD31, for example a CD31 protein fragment as described above, in a biological sample from a subject.

Also provided is are methods of diagnosis, including diagnosis of thrombosis such as on-going thrombosis and inflammatory conditions, said methods comprising detection of a platelet-derived shed ectodomain of CD31, for example a CD31 protein fragment as described above, in a biological sample from a subject. Exemplary methods of diagnosis are described herein.

A biological sample may for example correspond to plasma, blood or urine. The biological sample preferably corresponds to plasma. Most preferably, the biological sample is obtained from an individual suffering from or at risk of suffering from a thrombotic or an autoimmune disorder.

The inventors' finding now makes it possible to distinguish the different forms of soluble CD31. In particular, it is now possible to distinguish the platelet-derived form from the splice variant, as both comprise an epitope of the $6^{th}$ Ig-like domain but the intracellular domain is only present on the splice variant. This is a significant advance on the previously known methods, as the previously known shed forms of CD31 were not bound by antibodies to the $6^{th}$ Ig-like domain.

Thus, the invention further provides methods for detecting a platelet-derived shed ectodomain of a CD31 protein in a biological sample, for example a CD31 protein fragment as described above, among soluble forms of CD31 wherein said soluble forms include a soluble splice variant of said CD31 protein, which methods comprise the steps of:
a) providing a first discriminating antibody which specifically binds to an epitope located in a region that is present on said splice variant and on said platelet-derived shed ectodomain, which antibody is optionally labeled with a detectable label;
b) providing a second discriminating antibody which specifically binds to an epitope located in a region that is present on said splice variant and absent from said platelet-derived shed ectodomain, which antibody is optionally labeled with a detectable label;
c) optionally, providing a labeled detection ligand which specifically binds to a region that is present both on said shed ectodomain and on said splice variant;
d) measuring the signal obtained from said detectable label, optionally by flow cytometry;
wherein said detection ligand, where present, binds to a region within the $1^{st}$, $2^{nd}$, $3^{rd}$, $4^{th}$, $5^{th}$ or $6^{th}$ Ig-like extracellular domain of said CD31;
wherein said first discriminating antibody binds to the $6^{th}$ Ig-like extracellular domain of said CD31;
and wherein said second discriminating antibody binds to the intracellular domain of said CD31.

Also provided are methods for detecting a platelet-derived shed ectodomain of a CD31 protein in a biological sample, for example a CD31 protein fragment as described above, optionally among soluble forms of CD31 wherein said soluble forms include a soluble splice variant of said CD31 protein and optionally additional shed ectodomains, which methods comprise the steps of:
a) providing a capture antibody optionally immobilized on a solid support, wherein said capture antibody specifically binds to an epitope located in a region that is present both on said a platelet-derived shed ectodomain and on said splice variant;
b) providing a first discriminating antibody which specifically binds to an epitope located in a region that is present on said splice variant and on said platelet-derived shed ectodomain, which antibody is optionally labeled with a detectable label;
c) providing a second discriminating antibody which specifically binds to an epitope located in a region that is present on said splice variant and absent from said platelet-derived shed ectodomain, which antibody is optionally labeled with a detectable label;
   d) optionally, providing a labeled detection ligand which specifically binds to a region that is present both on said shed ectodomain and on said splice variant;
   contacting said antibodies with a biological sample likely to contain said soluble forms of said transmembrane protein;
   e) measuring the signal obtained from said detectable label, optionally by flow cytometry;
wherein said capture antibody and said detection ligand, where present, bind to a region within the $1^{st}$, $2^{nd}$, $3^{rd}$, $4^{th}$, $5^{th}$ or $6^{th}$ Ig extracellular domain of said CD31;
and wherein said first discriminating antibody binds to the intracellular domain of said CD31.

The invention also provides a method for detecting a platelet-derived shed ectodomain of a CD31 protein as described herein, a lymphocyte-derived shed ectodomain of a CD31 protein and a soluble splice variant of said CD31 protein in a biological sample, the method comprising:
   a) providing a capture antibody optionally immobilized on a solid support, wherein said capture antibody specifically binds to an epitope located in a region that is present on said platelet-derived shed ectodomain, on said lymphocyte-derived shed ectodomain and on said splice variant;
   b) providing a first discriminating antibody which specifically binds to an epitope located in a region that is present on said platelet-derived shed ectodomain and said splice variant and absent from said lymphocyte-derived shed ectodomain;
   c) providing a second discriminating antibody which specifically binds to an epitope located in a region that is present on said splice variant and absent from said platelet-derived shed ectodomain and from said lymphocyte-derived shed ectodomain;
   d) providing a third discriminating antibody specifically binds to an epitope located in a region that is present on said platelet-derived shed ectodomain, on said lymphocyte-derived shed ectodomain and on said splice variant;
wherein said discriminating antibodies are labeled with a detectable label, optionally a fluorescent label;
   e) contacting said antibodies with a biological sample likely to contain said soluble forms of said transmembrane protein;
   f) measuring the signal obtained from the label associated with each discriminating antibody, optionally by flow cytometry; and
   g) comparing the signal obtained for each discriminating antibody;
wherein the capture antibody and the third discriminating antibody bind within the region defined by the $1^{st}$, $2^{nd}$, $3^{rd}$, $4^{th}$ and $5^{th}$ extracellular domains of said CD31, the first discriminating antibody binds within the 6th Ig-like extracellular domain of said CD31, and the second discriminating antibody binds to the intracellular domain of said CD31.

Further provided is a method for detecting a platelet-derived shed ectodomain of a CD31 protein according to any one of claims 1 to 6, a lymphocyte-derived shed ectodomain of a CD31 protein and a soluble splice variant of said CD31 protein in a biological sample, the method comprising:
   a) providing a first support linked to a first antibody which specifically binds to an epitope located in a region that is present on said lymphocyte-derived shed ectodomain, on platelet-derived shed ectodomains, and on said splice variant,
   b) providing a second support linked to a second antibody which specifically binds to an epitope located in a region that is present on said platelet-derived shed ectodomain and said splice variant, bust absent from said lymphocyte-derived shed ectodomain;
   c) providing a third support linked to a third antibody which specifically binds to an epitope located in a region present in said splice variant, but absent from said platelet-derived shed ectodomain and said lymphocyte-derived shed ectodomain;
wherein all said antibodies are labeled with a detectable label, optionally a fluorescent label;
   d) contacting said antibodies with a biological sample;
   e) for each support, measuring the signal obtained with said label, optionally by flow cytometry; and optionally
   f) comparing the signal obtained for each support;
wherein said first antibody binds within the region defined by the $1^{st}$, $2^{nd}$, $3^{rd}$, $4^{th}$ and $5^{th}$ extracellular domains of said CD31;
and wherein said second antibody binds to the $6^{th}$ Ig-like extracellular domain of said CD31;
and wherein said third antibody binds to the intracellular domain.

Said support may be a bead, for example a cytometric bead.

Also provided is a method for detecting a platelet-derived shed ectodomain of a CD31 protein according to any one of claims 1 to 6, a lymphocyte-derived shed ectodomain of a CD31 protein and a soluble splice variant of said CD31 protein in a biological sample, the method comprising:
   a) providing a first support linked to a first antibody which specifically binds to an epitope located in a region that is present on said lymphocyte-derived shed ectodomain, on platelet-derived shed ectodomains, and on said splice variant,
   b) providing a second support linked to a second antibody which specifically binds to an epitope located in a region that is present on said platelet-derived shed ectodomain and said splice variant, bust absent from said lymphocyte-derived shed ectodomain;
   c) providing a third support linked to a third antibody which specifically binds to an epitope located in a region present in said splice variant, but absent from said platelet-derived shed ectodomain and said lymphocyte-derived shed ectodomain;
   d) optionally, providing a labelled detection ligand which specifically binds to an epitope located in a region that is present on said lymphocyte-derived shed ectodomain, on said platelet-derived shed ectodomais, and on said splice variant;
wherein in embodiments where a detection ligand is not used, said $1^{st}$, $2^{nd}$ and $3^{rd}$ antibodies are labeled with a detectable label;
   e) contacting said antibodies with a biological sample;
   f) for each support, measuring the signal obtained with said label by flow cytometry; and optionally
   g) comparing the signal obtained for each support;
wherein said first antibody and said detection ligand binds within the region defined by the $1^{st}$, $2^{nd}$, $3^{rd}$, $4^{th}$ and $5^{th}$ extracellular domains of said CD31;
and wherein said second antibody binds to the $6^{th}$ Ig-like extracellular domain of said CD31;
and wherein said third antibody binds to the intracellular domain.

The methods of the invention may further comprising the step of calculating the percentage and/or the amount of total soluble forms that correspond to platelet-derived shed ectodomain, and/or the step of calculating the ratio of platelet-derived shed ectodomain to soluble forms, and/or the step of calculating the percentage and/or the amount of splice variant that corresponds to platelet-derived shed ectodomain, and/or the step of calculating the ratio of platelet-derived shed ectodomain to splice variant, and/or the step of calculating the percentage and/or the amount of total soluble forms that corresponds to total shed ectodomains (platelet and lymphocyte-derived), and/or the step of calculating the ratio of total shed ectodomains to said soluble forms, and/or the step of calculating the percentage and/or the amount of total soluble forms that corresponds to said splice variant, and/or the step of calculating the ratio of splice variant to soluble forms.

Also provided is a method for monitoring the response of a patient to a drug, said method comprising the steps of:
a) detecting a platelet-derived shed ectodomain such as a CD31 as defined herein according to any one of claims 1 to 6 in a biological sample of said patient before and after onset of a treatment of said patient with said drug;
b) comparing the levels of the said ectodomain detected at step (a); and, optionally,
c) correlating a difference in the levels of said platelet-derived shed ectodomain with the effectiveness of the drug for treating said patient.

Also provided is a diagnostic kit comprising:
a) at least one antibody which specifically binds to an epitope located in a region that is present on said lymphocyte-derived shed ectodomain, on platelet-derived shed ectodomains, and on said splice variant;
b) at least one antibody which specifically binds to an epitope located in a region that is present on said platelet-derived shed ectodomain and said splice variant, but absent from said lymphocyte-derived shed ectodomain;
c) at least one antibody which specifically binds to an epitope located in a region present in said splice variant, but absent from said platelet-derived shed ectodomain and said lymphocyte-derived shed ectodomain.

Also provided is a diagnostic kit comprising:
a) a bead linked to an antibody that specifically binds to an epitope located in a region that is present in the $1^{st}$, $2^{nd}$, $3^{rd}$, $4^{th}$ or $5^{th}$ Ig-like extracellular domain of CD31;
b) a first labelled antibody that specifically binds to an epitope located in the $6^{th}$ extracellular immunoglobulin-like domain of CD31; and
c) a second labelled antibody that specifically binds to an epitope located in a region that is present in the $1^{st}$, $2^{nd}$, $3^{rd}$, $4^{th}$ or $5^{th}$ Ig-like extracellular domain of CD31;
d) a third labelled antibody that specifically binds to an epitope located in a region that is present in the intracellular domain or the juxtamembrane domain of said CD31.

CD31 (PECAM-1)

Full-length CD31 consists of a single chain molecule comprising 6 Ig-like extracellular domains, a short transmembrane segment and a cytoplasmic tail containing two ImmunoTyrosine-based Inhibitory Motif (ITIM)s. The sequence of full-length human CD31 is shown in FIG. 1 (SEQ ID NO: 1) The structure of CD31 is shown in Table 1 below.

TABLE 1

Domain structure of human CD31

| Domain | Position on SEQ ID No: 1 |
|---|---|
| Signal peptide | 1 to 27 |
| Extracellular domain | 28 to 601 |
| First Ig-like extracellular domain | 34 to 121 |

TABLE 1-continued

Domain structure of human CD31

| Domain | Position on SEQ ID No: 1 |
|---|---|
| Second Ig-like extracellular domain | 145 to 233 |
| Third Ig-like extracellular domain | 236 to 315 |
| Fourth Ig-like extracellular domain | 328 to 401 |
| Fifth Ig-like extracellular domain | 424 to 493 |
| Sixth Ig-like extracellular domain | 494 to 591 |
| Juxta-membrane domain | 592 to 601 |
| Transmembrane domain | 602 to 620 |
| Cytoplasmic (intracellular) domain | 621 to 738 |

Reference herein to the various domains of CD31 may refer to the domain locations as defined above or said locations +/−1, 2, 3, 4, 5, 6, 7, 8, 9, 10, 11, 12, 13, 14, 15, 16, 17, 18, 19, 20 or more amino acids.

Reference herein to 'at least a part of' the $6^{th}$ Ig-like domain may be the whole or a part of the $6^{th}$ Ig-like domain commencing at residue 494 and ending at residue 591, 590, 589, 588, 587, 586, 585, 584, 583, 582, 581, 580, 579, 578, 577, 576, 575, 574, 573, 572, 571, 570, 569, 568, 567, 566, 565, 564, 563, 562, 561, 560, 559, 558, 557, 556, 555, 554, 553, 552, 551, 550, 549, 548, 547, 546, 545, 544, 543, 542, 541, 540, 539, 538, 537, 536, 535, 534, 533, 532, 531, 530, 529, 528, 527, 526, 525, 524, 523, 522, 521, 520, 519, 518, 517, 516, 515, 514, 513, 512, 511, 510, 509, 508, 507, 506, 505, 504, 503, 502, 501, 500, 499, 498, 497, 496 or 495 of human CD31, as referred to in Table 1. For example, the protein of the invention may comprise a part of the $6^{th}$ Ig-like domain which comprises at least the amino acid sequence commencing at residue 494 and ending at residue 590, 589, 588, 587, 586, 585, 584, 583, 582, 581, 580, 579, 578, 577, 576, 575, 574, 573, 572, 571, 570, 569, 568, 567, 566, 565, 564, 563, 562, 561, 560, 559, 558, 557, 556, 555, 554, 553, 552, 551, 550, 549, 548, 547, 546, 545, 544, 543, 542, 541, 540, 539, 538, 537, 536, 535, 534, 533, 532, 531, 530, 529, 528, 527, 526, 525, 524, 523, 522, 521, 520, 519, 518, 517, 516, 515, 514, 513, 512, 511, 510, 509, 508, 507, 506, 505, 504, 503, 502, 501, 500, 499, 498, 497, 496 or 495 of human CD31.

As used herein, the term "CD31" refers to the molecule also referred to as CD31 antigen or PECAM-1. The protein may be of any origin, preferably of mammalian origin, and most preferably of human origin. In human, the gene coding for CD31 is located at locus 17q23. The full-length sequence of human CD31 is shown in FIG. 2 and SEQ ID No 1.

As used herein, the terms "platelet-derived shed ectodomain", "platelet-derived shed CD31", "platelet-derived shed form", "platelet-derived shed CD31", "platelet-derived soluble CD31" and "platelet-derived soluble form" and the like refer to a CD31 molecule which comprises Ig-like domains 1 to 5 and all or part of Ig-like domain 6 but does not comprise the intracellular domain, as described above. This molecule is cleaved from activated platelets.

As used herein, the terms "lymphocyte-derived shed ectodomain", "lymphocyte-derived shed CD31", "lymphocyte-derived shed form", "lymphocyte-derived shed CD31", "lymphocyte-derived soluble CD31" and "lymphocyte-derived soluble form" and the like refer to a CD31 molecule which comprises Ig-like domains 1, 2, 3, 4 and 5 but does not comprise Ig-like domain 6 or the juxtamembrane, transmembrane or intracellular domains, as described in PCT/EP2009/058220 (WO2010/000756). This molecule is cleaved from activated T-lymphocytes.

As used herein, the terms "soluble splice variant", "splice variant", "splice variant of CD31" and the like refer to a CD31 molecule which does not comprise the transmembrane domain, as described in Goldberger al al (1994); J Biol Chem 269, 17183-17191. Said molecule comprises the intracellular domain and all or most of Ig-like domains 1, 2, 3, 4, 5 and 6. This molecule is secreted from endothelial cells.

The sequence of human wild-type CD31 is shown as SEQ ID NO: 1. However, the invention also relates to allelic variants thereof, and to the homologues thereof in other species.

Variant proteins may be naturally occurring variants, such as splice variants, alleles and isoforms, or they may be produced by recombinant means. Variations in amino acid sequence may be introduced by substitution, deletion or insertion of one or more codons into the nucleic acid sequence encoding the protein that results in a change in the amino acid sequence of the protein. Optionally the variation is by substitution of 1, 2, 3, 4, 5, 6, 7, 8, 9, 10, 11, 12, 13, 14, 15, 16, 17, 18, 19, 20 or more amino acids with any other amino acid in the protein. Amino acid substitutions may be conservative or non-conservative. Preferably, substitutions are conservative substitutions, in which one amino acid is substituted for another amino acid with similar structural and/or chemical properties. Additionally or alternatively, the variation may be by addition or deletion of 1, 2, 3, 4, 5, 6, 7, 8, 9, 10, 11, 12, 13, 14, 15, 16, 17, 18, 19, 20 or more amino acids within the protein.

Amino acid substitutions may be conservative or non-conservative. Preferably, substitutions are conservative substitutions, in which one amino acid is substituted for another amino acid with similar structural and/or chemical properties. Exemplary conservative substitutions are listed below.

Ala (A) val; leu; ile
Arg (R) lys; gin; asn
Asn (N) gln; his; lys
Asp (D) glu
Cys (C) ser
Gln (Q) asn
Glu (E) asp
Gly (G) pro; ala
His (H) asn; Gln; lys; arg
He (I) leu; val; met; ala
norleucine leu
Leu (L) norleucine; ile; met; ala; phe
Lys (K) arg; Gln; asn
Met (M) leu; phe; ile
Phe (F) leu; val; ile; ala; tyr
Pro (P) ala
Ser (S) thr
Thr (T) ser
Trp (W) tyr; phe
Tyr (Y) trp; phe; thr; ser
Val (V) ile; leu; met; phe; ala; norleucine Variant proteins may include proteins that have at least about 80% amino acid sequence identity with a polypeptide sequence disclosed herein. Preferably, a variant protein will have at least about t 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a full-length polypeptide sequence or a fragment of a polypeptide sequence as disclosed herein. Amino acid sequence identity is defined as the percentage of amino acid residues in the variant sequence that are identical with the amino acid residues in the reference sequence, after aligning the sequences and introducing gaps, if necessary, to achieve the maximum percent sequence identity, and not considering any conservative substitutions as part of the sequence identity. Sequence identity may be determined over the full length of the variant sequence, the full length of the reference sequence, or both.

Variant nucleic acid sequences may include nucleic acid sequences that have at least about 80% amino acid sequence identity with a nucleic acid sequence disclosed herein. Preferably, a variant nucleic acid sequences will have at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a full-length nucleic acid sequence or a fragment of a nucleic acid sequence as disclosed herein. Nucleic acid acid sequence identity is defined as the percentage of nucleic acids in the variant sequence that are identical with the nucleic acids in the reference sequence, after aligning the sequences and introducing gaps, if necessary, to achieve the maximum percent sequence identity, and not considering any conservative substitutions as part of the sequence identity. Sequence identity may be determined over the full length of the variant sequence, the full length of the reference sequence, or both.

Methods for sequence alignment and determination of sequence identity are well known in the art, for example using publicly available computer software such as BioPerl, BLAST, BLAST-2, CS-BLAST, FASTA, ALIGN, ALIGN-2, LALIGN, Jaligner, matcher or Megalign (DNASTAR) software and alignment algorithms such as the Needleman-Wunsch and Smith-Waterman algorithms.

For example, the percentage identity may be calculated by performing a pairwise global alignment based on the Needleman-Wunsch alignment algorithm to find the optimum alignment (including gaps) of two sequences along their entire length, for instance using Needle, and using the BLOSUM62 (for amino acid sequences) or the DNAfull matrix (for nucleic acid sequences) matrix with a gap opening penalty of 10 and a gap extension penalty of 0.5.

Fragments of the proteins and variant proteins disclosed herein are also included. Such fragments may be truncated at the N-terminus or C-terminus, or may lack internal residues, for example, when compared with a full length protein. Certain fragments lack amino acid residues that are not essential for enzymatic activity. Preferably, said fragments are at least about 10, 20, 30, 40, 50, 60, 70, 80, 90, 100, 110, 120, 150, 250, 300, 350, 400, 450, 500 or more amino acids in length, and/or not more than 10, 20, 30, 40, 50, 60, 70, 80, 90, 100, 110, 120, 150, 250, 300, 350, 400, 450, 500 amino acids in length Fragments of the nucleic acid sequences and variants disclosed herein are also included. Such fragments may be truncated at 3' or 5' end, or may lack internal bases, for example, when compared with a full length nucleic acid sequence. Preferably, said fragments are at least about 10, 20, 30, 40, 50, 60, 70, 80, 90, 100, 110, 120, 150, 250, 300, 350, 400, 450, 500, 600, 700, 800, 900, 1000, 1500 or more bases in length, and/or not more than 10, 20, 30, 40, 50, 60, 70, 80, 90, 100, 110, 120, 150, 250, 300, 350, 400, 450, 500, 600, 700, 800, 900, 1000, 1500 bases in length.

The term "fragment" of a reference sequence refers to a chain of contiguous nucleotides or amino acids that is shorter than the reference sequence. The CD31 fragments may have a length of 10, 20, 30, 40, 50, 60, 70, 80, 90, 100, 110, 120, 150, 250, 300, 350, 400, 450, 500 or more amino acids in length, and/or not more than 10, 20, 30, 40, 50, 60, 70, 80, 90, 100, 110, 120, 150, 250, 300, 350, 400, 450, 500 amino acids in length Antibodies The methods of the invention use antibodies which bind to the various forms of CD31, as described above. The term 'antibody' is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term 'monoclonal antibody' as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier 'monoclonal' indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

Unless indicated otherwise, the expression 'multivalent antibody' denotes an antibody comprising three or more antigen binding sites. In certain embodiment, the multivalent antibody is engineered to have the three or more antigen binding sites and is generally not a native sequence IgM or IgA antibody.

'Antibody fragments' comprise a portion of an intact antibody, preferably comprising the antigen binding region thereof. Examples of antibody fragments include Fab, Fab', F(ab')2, and Fv fragments; diabodies; linear antibodies; single-chain antibody molecules; and multispecific antibodies formed from antibody fragments. 'Fv' is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a 'dimeric' structure analogous to that in a two-chain Fv species. It is in this configuration that the three HVRs of each variable domain interact to define an antigen-binding site on the surface of the VH-VL dimer.

Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term 'hypervariable region,' 'HVR,' or 'HV,' when used herein refers to the regions of an antibody variable domain which are hypervariable in sequence and/or form structurally defined loops. Generally, antibodies comprise six HVRs; three in the VH (HI, H2, H3), and three in the VL (LI, L2, L3). In native antibodies, H3 and L3 display the most diversity of the six HVRs, and H3 in particular is believed to play a unique role in conferring fine specificity to antibodies. See, e.g., Xu et al, Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

'Framework' or 'FR' residues are those variable domain residues other than the HVR residues as herein defined.

The term 'Fc region' herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A 'functional Fc region' possesses an 'effector function' of a native sequence Fc region. Exemplary 'effector functions' include Clq binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A 'native sequence Fc region' comprises an amino acid sequence identical to the amino acid sequence of an Fc region found in nature. Native sequence human Fc regions include a native sequence human IgGI Fc region (non-A and A allotypes); native sequence human IgG2 Fc region; native sequence human IgG3 Fc region; and native sequence human IgG4 Fc region as well as naturally occurring variants thereof.

A 'variant Fc region' comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

'Fc receptor' or 'FcR' describes a receptor that binds to the Fc region of an antibody An antibody which "specifically binds" to a target protein binds to said target protein with greater affinity and/or avidity that to other proteins or epitopes, even closely related proteins or epitopes. Preferably, an antibody which specifically binds to a specific soluble CD31 form as described herein, binds to said form with greater affinity and/or avidity than it binds to other soluble CD31 forms. Most preferably, an antibody which specifically binds to a specific soluble CD31 form as described herein does not bind to other soluble CD31 forms.

Typically, the antibody binds to its target protein with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by surface plasmon resonance (SPR) technology in a BIAcore 3000 instrument using recombinant CD38 as the ligand and the antibody as the analyte. The antibody may bind to the target with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g. other soluble CD31 forms, BSA, casein). The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The phrases "an antibody recognizing an antigen" and "an antibody specific for an antigen" are used interchangeably herein with the term "an antigen binding peptide which binds specifically to an antigen". Likewise, the phrases "an antibody recognizing an antigen" and "an antibody specific for an antigen" are used interchangeably herein with the term "an antibody which binds specifically to an antigen".

The term "$k_d$" ($sec^{-1}$), as used herein, is intended to refer to the dissociation equilibrium rate constant of a particular antibody-antigen interaction. Said value is also referred to as the $k_{off}$ value.

The term "$k_a$" ($M^{-1} \times sec^{-1}$), as used herein, is intended to refer to the association equilibrium rate constant of a particular antibody-antigen interaction.

The term "$K_D$" (M), as used herein, is intended to refer to the dissociation equilibrium constant of a particular antibody-antigen interaction.

The term "$K_A$" ($M^{-1}$), as used herein, is intended to refer to the association equilibrium constant of a particular antibody-antigen interaction and is obtained by dividing the $k_a$ by the $k_d$.

By "ligand" is meant a natural ligand, an antibody or an aptamer. The ligand preferably is an antibody that specifically binds to an epitope located in a region that is present both on the shed ectodomain and on the splice variant.

An antibody, in particular a detection antibody, or a detection ligand may be labeled. Preferably, the label is a detectable label, such as a fluorescent label. Fluorescent labels known in the art such include. FITC (FL1), PE (FL2), fluorophores for use in the blue laser (e.g. PerCP, PE-Cy7, PE-Cy5, FL3 and APC or Cy5, FL4), fluorophores for use in the red, violet or uv laser (e.g. Pacific blue, pacific orange). Optimized methods include different emission spectra for the beads and the detecting antibodies. The antibody is preferably directly labelled. However, it may also be indirectly labelled, especially when the antibody is a polyclonal antibody.

In certain embodiments, an antibody or ligand, in particular a capture antibody, may be immobilised on a solid support. Solid supports suitable for use in the method of invention are widely known to one of skill in the art. It is not intended that the present invention be limited to any particular type of solid support material or configuration.

Solid supports can be flat or planar, or can have substantially different conformations. For example, the solid support can exist as particles, beads, strands, precipitates, gels, sol-gels, sheets, tubing, spheres, containers, columns, capillaries, pads, slices, films, plates, dipsticks, slides, etc. For example, microplates could be used, in particular polystyrene microplates, such as those sold by Nunc, Denmark. Solid particles or beads, magnetic or paramagnetic beads or particles such as those produced by Dynal, Merck-Eurolab (France) (under the trademark Estapor™) and Polymer Laboratories, are particularly preferred. Magnetic particles are described in, for example, U.S. Pat. No. 4,672,040, and are commercially available from, for example, PerSeptive Biosystems, Inc. (Framingham Mass.), Ciba Corning (Medfield Mass.), Bangs Laboratories (Carmel Ind.), and BioQuest, Inc. (Atkinson N.H.). Agarose or other gel-type beads may also be used, such as Pierce CDI-activated beads. Polystyrene or polypropylene test tubes, glass, plastic or silicon chips, etc. may also be used. A preferred bead is a cytometric bead for use in flow cytometry. In the method according to the invention, different types of beads refer to beads distinguishable from each other. Such beads may for example correspond to BD™ Cytometric Beads commercialized by BD Biosciences (San Jose, Calif.). Beads are well-known in the art.

Exemplary solid support materials include glasses or other ceramics, plastics, polymers, metals, metalloids, alloys, composites, organics. The solid support is chosen to maximize signal to noise ratios, primarily to minimize background binding, for ease of washing and cost. In addition, certain solid supports such as beads can easily be used in conventional fluid handling systems such as microwell plates. The separation of materials that can be achieved by such conventional fluid handling systems can be used to construct arrays according to the present invention, e.g., to provide beads comprising different un-natural amino acid-containing polypeptides, or contact with different reagents, or both.

Therefore, the invention relates to a method for detecting a platelet-derived shed ectodomain of CD31 among soluble forms of CD31 in a biological sample wherein at least two discriminating antibodies are used, domain of CD31, one specifically binding to an epitope located in the intracellular domain of CD31 and another one specifically binding to an epitope located in the sixth extracellular immunoglobulin-like domain of CD31. An antibody specifically binding to an epitope located in any of the first five extracellular immunoglobulin-like domains (domains 1, 2, 3, 4 and 5) of CD31 may also be used, either as a capture or a discriminating antibody. The capture or signaling ligand binding to all soluble forms may for example specifically bind to the first and/or second extracellular immunoglobulin-like domains of CD31. The capture or signaling ligand is preferably a capture or signaling antibody, which may for example specifically bind to an epitope located in the first and/or second extracellular immunoglobulin-like domains of CD31. Such antibodies are well-known in the art and may for example correspond to any one of the antibodies listed in the HLDA Antibody Database (see world wide web page 99.mh-hannover.de/aktuelles/projekte/hlda7/hldabase/CD31.htm).

As used herein, the term "epitope located in the sixth extracellular immunoglobulin-like domain of CD31" refers to an epitope located within amino acids 494 to 591 of SEQ ID NO: 1, i.e. within the sixth extracellular immunoglobulin-like domain of CD31 (amino acids 494 to 591 of SEQ ID NO: 1). In some embodiments, said term may also encompass epitopes located within the juxta-membrane region (amino acids 592 to 601 of SEQ ID NO: 1). Preferably, said epitopes are located within amino acids 499 to 591, 524 to 601 or 524 to 538 of SEQ ID NO: 1. In some embodiments, the antibody which specifically binds to an epitope located in the sixth extracellular immunoglobulin-like domain of CD31 corresponds to the PECAM 1.2 antibody (Invitrogen, San Diego, Calif.), the PECAM1.1 antibody, or the HCl/6 antibody (Serotec, Kidlington, UK, or MBC78.2 (directed against human CD31 domain 6), and/or the "epitope located in the sixth extracellular immunoglobulin-like domain of CD31" may correspond to the epitope bound by any of these antibodies. The PECAM 1.2 antibody has been described e.g. in Yan et al. (Cell Adhes Commun 3:45-66).

Positive binding of soluble CD31 will be detected by four other anti-CD31 monoclonal antibody, coupled to FITC, PE, PerCP-Cy5.5 and BD Horizon® V450.

As used herein, the term "epitope located in either of the first five extracellular immunoglobulin-like domain of CD31" refers to an epitope located within amino acids 28 to 493 of SEQ ID NO: 1, most preferably within amino acids 34 to 493 of SEQ ID NO: 1. In preferred embodiments according to the invention, said epitope is located in the fifth extracellular immunoglobulin-like domain of CD31, or in the first and/or second extracellular immunoglobulin-like domain of CD31.

As used herein, the term "epitope located in the fifth extracellular immunoglobulin-like domain of CD31" refers to an epitope located within amino acids 424 to 493 of SEQ ID NO: 1. Preferably, said epitopes are located within amino acids 448 to 470 of SEQ ID NO: 1. In a preferred embodiment, the antibody which specifically binds to an epitope located in the fifth extracellular immunoglobulin-like domain of CD31 is the MEM-05 antibody (Exbio Praha, Czech Republic) or the MBC78.1 antibody.

As used herein, the term "epitope located in the first and/or second extracellular immunoglobulin-like domain of CD31" refers to an epitope located within amino acids 34 to 233 of SEQ ID NO: 1. An epitope located in the first extracellular immunoglobulin-like domain of CD31 is preferably located within amino acids 49 to 68 of SEQ ID NO: 1. An epitope located in the second extracellular immunoglobulin-like domain of CD31 is preferably located within amino acids 166 to 187 of SEQ ID NO: 1. In a preferred embodiment, the antibody which specifically binds to an epitope located in the first two extracellular immunoglobulin-like domains of CD31 corresponds to the WM59 antibody (domain 2, BD, San Jose, Calif.), to the JC70A antibody (domain 1, DAKO, Glostrup, Denmark), MBC78.3 (domain 2) or to the 9G11 antibody (domain 1, R&D systems, Minneapolis, USA). The WM59 and JC70A antibodies have been described e.g. in Fawcett et al. (J Cell Biol 128:1229-1241).

As used herein, the term "epitope located in the intracellular domain of CD31" refers to an epitope located within amino acids 621 to 738 of SEQ ID NO: 1. Antibodies which bind to an epitope located in the intracellular domain of CD31 include the mouse monoclonal antibody MBC 235.1 and the rabbit monoclonal antibody SP38 (Spring Bioscience/Abcam).

Said soluble forms of the transmembrane protein may include additional soluble forms corresponding to e.g. additional soluble splice variants, additional shed ectodomains, or to variants generated by proteolytic processing. When the soluble forms include at least three soluble forms, more than two discriminating antibodies may be used. Within this embodiment, the discriminating antibodies are chosen in such a way as to discriminate between the soluble forms, and the capture or signaling antibody specifically binds to an epitope located in a region that is present on all said soluble forms.

The method for detecting of a platelet-derived shed ectodomain of CD31 may further comprise the step of calculating the proportion, percentage and/or amount of said soluble forms that corresponds to said platelet-derived shed ectodomain of CD31, and/or the step of comparing the measured signals with those obtained with at least one biological sample comprising known amounts of said platelet-derived shed ectodomain and of said soluble splice variants. The method for detecting of a platelet-derived shed ectodomain of CD31 preferably comprises the step of calculating the ratio of platelet-derived shed ectodomain to total soluble forms, i.e. the ratio of platelet-derived shed CD31 to all soluble isoforms (soluble isoform comprising domains 1-6, soluble isoform comprising domains 1-5, and soluble isoform comprising domains 1-2).

FIG. 3 illustrates a method in accordance with the invention for the detection and quantification of the various soluble forms of CD31. Beads linked to antibodies specifically binding to epitopes located in the $1^{st}$ Ig-like domain are used to pull down total soluble CD31. Labelled discriminating antibodies detecting the $2^{nd}$ and/or $5^{th}$ and the $6^{th}$ extracellular Ig-like domain and the intracellular domain are used.

The signals obtained for each antibody correspond to the different forms as follows:

$aCD31_{int}$=Soluble splice variant
$aCD31_{d6}$=Soluble splice variant+platelet-derived shed ectodomain
$aCD31_{d5}$, $aCD31_{d2}$=Soluble splice variant+platelet-derived shed ectodomain+lymphocyte-derived shed ectodomain Thus, a simple subtractive calculation based on measurement of the intensity of the signal obtained for each antibody allows quantifying the respective proportion of each of the soluble forms of CD31:

Soluble splice variant=$aCD31_{int}$
Platelet-derived shed ectodomain=$aCD31_{int}$-$aCD31_{d6}$
Lymphocyte-derived shed ectodomain=$aCD31_{d5}$-$aCD31_{d6}$
Lymphocyte-derived shed ectodomain=$aCD31_{d2}$-$aCD31_{d6}$ The above methods may further comprise the step of calculating the proportion, percentage and/or amount of said soluble forms that corresponds to said platelet-derived shed ectodomain, and/or the step of comparing the measured signals with those obtained with at least one biological sample comprising known amounts of said platelet-derived shed ectodomain and of said soluble forms, and/or the step of calculating the ratio of platelet-derived shed ectodomain (and/or lymphocyte-derived shed ectodomain and/or spliced form) to soluble forms (i.e. all soluble isoforms or "total soluble forms"). The methods for detecting soluble forms of CD31 find use both in analytical and diagnostic applications. Some of the diagnostic applications are described in more details in the paragraph herebelow.

Specific Detection of Platelet-Derived Shed Ectodomain of CD31

Methods for detection of a platelet-derived shed ectodomain of a CD31 protein are described above. Other methods encompassed by the invention are also envisaged and are described below.

Also provided is a method for detecting a platelet-derived shed ectodomain of a CD31 protein among soluble forms of said protein in a biological sample, which platelet-derived shed ectodomain is a CD31 fragment as defined in any one of claims 1 to 6, wherein said soluble forms include a soluble splice variant of said CD31 protein and optionally additional shed ectodomains, which comprises the steps of:
 a) providing a first antibody linked to a solid support, which specifically binds to an epitope located in a region that is present both on said shed ectodomain and on said splice variant (first discriminating antibody);
 b) providing at least one second antibody linked to a solid support, which specifically binds to an epitope located in a region that is either present on said shed ectodomain and absent from said splice variant, or present on said splice variant and absent from said shed ectodomain (second discriminating antibody);
 c) providing a fluorescently-labelled ligand which specifically binds to a region that is present both on said shed ectodomain and on said splice variant (signaling ligand);
 d) contacting said antibodies with a biological sample likely to contain said soluble forms of said transmembrane protein;
 e) for each type of antibody, measuring the signal obtained with said florescent label; and
 f) comparing the signal obtained for each antibody.

A difference in the signals measured at step (f) indicates that the biological sample comprises said platelet-derived shed ectodomain of CD31, as described herein.

The first discriminating antibody preferably binds to the 6th Ig-like extracellular domain of said CD31 and the second discriminating antibody preferably binds to the intracellular domain of said CD31.

In a preferred embodiment, the signal obtained with said fluorescent label is measured by flow cytometry. Preferably, the biological sample is first contacted with the bead-linked antibodies, the beads are then recovered and contacted with the fluorescently-labelled ligand.

The method may further comprise detection of a lymphocyte-derived shed ectodomain. Thus, also provided is a method which comprises the steps of:
 a) providing a first antibody linked to a solid support, which specifically binds to an epitope located in a region that is present both on said lymphocyte-derived shed ectodomain, said platelet-derived shed ectodomain and shed ectodomain and on said splice variant (first discriminating antibody);
 b) providing at least one second antibody linked to a solid support, which specifically binds to an epitope located in a region that is present on said platelet-derived shed ectodomain and said splice variant, and absent from said lymphocyte-derived shed ectodomain (second discriminating antibody);
 c) providing at least one third antibody linked to a solid support, which specifically binds to an epitope located in a region that is present on said splice variant and absent from said shed ectodomains (third discriminating antibody);
 d) providing a fluorescently-labelled ligand which specifically binds to a region that is present both on both said shed ectodomains and on said splice variant (signaling ligand);
 e) contacting said antibodies with a biological sample likely to contain said soluble forms of said transmembrane protein;
 f) for each type of antibody, measuring the signal obtained with said florescent label by flow cytometry; and
 g) comparing the signal obtained for type of antibody.

A difference in the signals measured at step (g) indicates that the biological sample comprises said platelet-derived shed ectodomain of CD31 and/or said lymphocyte-derived shed ectodomain of CD31, as described herein.

The first discriminating antibody preferably binds within the $1^{st}$ to $5^{th}$ extracellular domains of CD31, the second discriminating antibody preferably binds within the 6th Ig-like extracellular domain of said CD31 and the third discriminating antibody preferably binds to the intracellular domain of said CD31.

Detection Methods

The present inventors' identification of a platelet-derived shed ectodomain allows the development of methods for differentiating between the different soluble isoforms of CD31. One such method is based on the use of a capture antibody immobilized on a solid support which recognizes all of the soluble forms of CD31. The captured antibodies are then detected with labeled antibodies which recognize all forms of soluble CD31 (lymphocyte, endothelial and platelet-derived). Alternatively, a labeled detection ligand which binds to all soluble forms may be used for detection.

The detectable labels may be detected by flow cytometry. Preferably, the biological sample is first contacted with the bead-linked antibodies, the beads are then recovered and contacted with the labelled ligand. Flow cytometers enable the characterization of particles on the basis of light scatter and particle fluorescence. In a flow cytometer, particles are individually analyzed by exposing each particle to an excitation light, typically one or more lasers, and the light scattering and fluorescence properties of the particles are measured. Particles, such as molecules, analyte-bound beads, individual cells, or subcomponents thereof, typically are labelled with one or more spectrally distinct fluorescent dyes, and detection is carried out using a multiplicity of photodetectors, one for each distinct dye to be detected. Flow cytometers are commercially available from, for example, BD Biosciences (San Jose, Calif.). Early in the development of flow cytometry, it was recognized that various types of ligand binding assays could be carried out using beads (also referred to as microparticles) coated with one member of a binding pair. The coated beads and reporters are incubated with a sample containing (or suspected of containing) the analyte of interest to allow for the formation of bead-analyte-reporter complexes. Analysis by flow cytometry enables both detecting the presence of bead-analyte-reporter complexes and simultaneously measuring the amount of reporter fluorescence associated with the complex as a quantitative measure of the analyte present in the sample. It was also recognized early in the development of flow cytometry that the simultaneous analysis of multiple analytes in a sample could be carried out using a set of distinguishable beads, each type of bead coated with a unique analyte-specific binding agent. The bead set and fluorescently labelled reporter reagents, one for each species of analyte to be detected, are incubated with a sample containing the analytes of interest to allow for the formation of bead-analyte-reporter complexes for each analyte present, and the resulting complexes are analyzed by flow cytometry to identify and, optionally, quantify the analytes present in the sample. Because the identity of the analyte bound to the complex is indicated by the identity of the bead, multiple analytes can be simultaneously detected using the same fluorophore for all reporter reagents.

A number of methods of making and using sets of distinguishable microparticles have been described in the literature. These include beads distinguishable by size, wherein each size microparticle is coated with a different target-specific antibody (see e.g. Fulwyler and McHugh, 1990, Methods in Cell Biology 33:613-629), beads with two or more fluorescent dyes at varying concentrations, wherein the beads are identified by the levels of fluorescence dyes (see e.g. European Patent No. 0 126,450), and beads distinguishably labelled with two different dyes, wherein the beads are identified by separately measuring the fluorescence intensity of each of the dyes (see e.g. U.S. Pat. Nos. 4,499,052 and 4,717,655).

Both one-dimensional and two-dimensional arrays for the simultaneous analysis of multiple analytes by flow cytometry are available commercially. Examples of one-dimensional arrays of singly dyed beads distinguishable by the level of fluorescence intensity include the BD™ Cytometric Bead Array (CBA) (BD Biosciences, San Jose, Calif.) and Cyto-Plex™ Flow Cytometry microspheres (Duke Scientific, Palo Alto, Calif.). An example of a two-dimensional array of beads distinguishable by a combination of fluorescence intensity (five levels) and size (two sizes) is the QuantumPlex™ microspheres (Bangs Laboratories, Fisher, Ind.). An example of a two-dimensional array of doubly-dyed beads distinguishable by the levels of fluorescence of each of the two dyes is described in Fulton et al. (1997, Clinical Chemistry 43(9):1749-1756).

Diagnostic Methods

Pathologic platelet activation and aggregation is responsible for acute thrombotic occlusion of small and medium sized arteries. Occlusion of coronary arteries may lead to myocardial infarction, occlusion of cerebral arteries to stroke, occlusion of peripheral arteries to mesenteric infarction, splenic infarction or acute limb ischemia. Thus, platelet activation and aggregation may play a role in all of these conditions, as well as other thrombotic conditions. In addition, platelets are a very rich source of inflammatory mediators, thus contributing to the amplification and dissemination of chronic inflammatory diseases. The reasons for this are not fully understood but may include uptake from extraplatelet space in inflammatory sites and small platelet emboli that enter the circulation from one such inflammatory site to release their proinflammatory content elsewhere. This is typically the case in atherosclerotic diseases and other inflammatory diseases including autoimmune conditions, such as rheumatoid arthritis (Science 29 January 2010, Vol. 327 no. 5965 pp. 528-529), in Crohn's disease (Danese S, de la Motte C, Fiocchi C. Platelets in inflammatory bowel disease: clinical, pathogenic, and therapeutic implications. Am J Gastroenterol 2004; 99:938-945) and multiple sclerosis (Journal of Neuroinflammation 2008, 5:27 doi:10.1186/1742-2094-5-27). Thus, the ability to detect platelet-derived shed CD31 may aid in the choice of appropriate treatment for patients suffering from such diseases.

The invention therefore provides a method for diagnosing whether an individual suffers, or is at risk of suffering, from a thrombotic or an inflammatory disorder, which comprises a step of detecting a platelet-derived shed ectodomain of CD31 in a biological sample of said individual, wherein the presence of said platelet-derived shed ectodomain of CD31 indicates that said individual suffers from or is at risk of suffering from said thrombotic or autoimmune disorder. Where platelet-derived shed ectodomain of CD31 is detectable, the method may further comprise the step of calculating the ratio of platelet-derived shed ectodomain to total soluble forms.

The invention further provides a method for diagnosing whether an individual suffers, or is at risk of suffering, from ongoing thrombosis orother thrombotic or inflammatory disorder, which comprises the steps of:
  a) providing a biological sample of said individual;
  b) detecting the platelet-derived shed ectodomain of CD31, for example according to any of the methods described herein in said biological sample; and
  c) optionally, correlating the result of step (b) with a risk of suffering from said disorder;
wherein the presence of said platelet-derived shed ectodomain of CD31 in said biological sample indicates that said individual suffers from or is at risk of suffering from said disorder.

The method may additionally comprise detection of lymphocyte-derived shed ectodomain.

The presence of at least 50%, 60%, 65%, 70%, 75%, 80%, 90% or 95% of platelet-derived shed ectodomain in the soluble forms of CD31, or the presence of at least 50%, 60%, 65%, 70%, 75%, 80%, 90% or 95% of platelet and lymphocyte-derived shed ectodomain in the soluble forms of CD31 may indicate that said individual suffers from or is at risk of suffering from a thrombotic or an inflammatory disorder.

The invention further provides a method of selecting a suitable treatment for an individual suffering from a thrombotic or inflammatory disorder, the method comprising a step of detecting a platelet-derived shed ectodomain of CD31 in a biological sample of said individual. The method may further comprise detection of lymphocyte-derived shed ectodomain of CD31 and/or soluble splice variant of CD31. The method may further comprise the step of calculating the relative levels of said soluble forms and/or the ratio of platelet-derived shed ectodomain to lymphocyte-derived shed ectodomain, the ratio of platelet-derived shed ectodomain to soluble splice variant and/or the ratio of platelet-derived shed ectodomain to total soluble forms.

An appropriate treatment regimen may then be selected for said individual. For instance, if an abnormally low level of soluble splice variant (i.e. endothelial CD31) is found in a patient with atherosclerosis, this indicates the use of treatment with Nitric Oxide derivatives, as NO is a main protective agent released by a healthy endothelium and contributing to several homeostatic functions in vasculatures of the body. Alternatively, in RA patients, an increase in the platelet-derived soluble form compared to the lymphocyte form may indicate use of antiplatelet agents rather than dangerously increasing the doses of the immunosuppressors in RA patients.

As used herein, the term "inflammatory disorder" includes but is not limited to autoimmune and thrombotic disorders such as those described below, rheumatic diseases, neuropathic pain, visceral disorders, allergy, asthma, eczema and psoriasis.

The term "thrombotic disorder" includes but is not limited to atherothrombosis, atherosclerosis, acute coronary syndrome, ongoing (chronic) thrombosis, ischemic stroke, splenic infarction, myocardial infarction, mesenteric infarction, acute limb ischemia peripheral arterial disease and abdominal aortic aneurysm.

The term "autoimmune disorder" includes but is not limited to rheumatoid arthritis (IRA), spondyloarthritis, multiple sclerosis (MS), inflammatory bowel disease (IBD), Crohn's disease, systemic lupus erythematodes (SLE), Graves' disease and diabetes mellitus.

The detection of said soluble forms of CD31 may be performed according to any method known in the art. It may for example be detected by one of the methods described in the above paragraph.

The biological sample may for example correspond to plasma, blood or urine. The biological sample preferably corresponds to plasma.

The diagnostic method in accordance with the invention may be repeated at least at two different points in time in order to monitor the progression of a thrombotic or an autoimmune disorder in the individual and/or to assess the severity of said disorder in said individual, and/or to monitor the response of the individual to a drug.

As used herein, events occurring at "a different (or later) point in time" refer to events occurring at an interval of at least 1 hour. Preferably, the events occur at an interval of at least 6 hours, 12 hours, 1 day, one week, two weeks or one month.

In a preferred embodiment, the amount and/or percentage of a given soluble form in a biological sample of said individual to be diagnosed is compared to the amount and/or percentage of said form in a biological sample of a healthy individual.

High levels of CD31 soluble splice variants associated with low levels of shed CD31 may indicates that the individual to be diagnosed suffers from non specific chest pain, eventually associated with carotid plaques. A slight increase of shed CD31 levels associated with normal or reduced levels of CD31 soluble splice variants may indicates that the individual to be diagnosed suffers from atherosclerosis. A larger increase of shed CD31 levels associated with undetectable amounts of CD31 soluble splice variants indicates that the individual to be diagnosed suffers from atherothrombosis.

The diagnostic methods in accordance with the invention may be used e.g. to determine whether an individual suffers from a thrombotic or an autoimmune disorder, to assess the severity of a thrombotic or an autoimmune disorder in an individual, to predict the risk of major cardiovascular events, such as recurrence of a myocardial infarction, to design a treatment regimen, to monitor the progression of a thrombotic or an autoimmune disorder in a patient, to predict and to monitor the response of a patient to a drug and/or to adjust the treatment of a patient.

When the diagnostic method in accordance with the invention is used to monitor the progression of a disorder, to assess the severity of a disorder, to monitor the response to a drug and/or to adjust the treatment of a patient, it carried out on biological samples taken from a given patient at different points in time. Biological samples may for example be taken each month in order to follow the patient's response to a treatment. Based on these analyses, the treatment may then be adjusted. It may for example be decided to change the drug, or to adjust the dosage of the drug in order to enhance its efficacy and/or minimize the side effects. Such a drug monitoring is especially advisable in long-term treatments, for example when a immunosuppressant compound is administered to a patient. Detecting shed CD31 can be used to monitor the inflammatory response in the patient, and thus to determine the minimal effective dose of drug that can be administered to the patient.

The invention therefore provides a method for monitoring the progression of a thrombotic or an autoimmune disorder, and/or for assessing the severity of a thrombotic or an autoimmune disorder in an individual, and/or for monitoring the response of a patient to a drug comprising the steps of:
  a) providing a first biological sample of said patient;
  b) detecting platelet-derived shed ectodomain, lymphocyte-derived shed ectodomain and/or soluble splice variant of CD31 in said first biological sample as described above;
  c) providing at least one second biological sample of said patient, wherein said at least one second biological sample has been taken from said patient at a later point in time than the first biological sample;
  d) detecting platelet-derived shed ectodomain, lymphocyte-derived shed ectodomain and/or soluble splice variant of CD31 in said at least one second biological sample as described above;
  e) comparing the results obtained at steps (b) and (d).

Several different biological samples, taken from the same patient at different points in times, may be used at steps (c), (d) and (e). For example, in the context of a long-term treatment of the patient, biological samples may be taken from the patient at regular intervals (e.g. each month, every two months or twice a year).

Such a method for monitoring the progression of a thrombotic or an autoimmune disorder; and/or to assess the severity of said disorder; and/or for monitoring the response of a patient to a drug may further comprise a step (f) of designing a treatment regimen for said patient based on the results of step (e).

In the frame of drug monitoring, the biological sample of step (a) is preferably taken before onset of the treatment of the patient, and the biological sample of step (c) after onset of the treatment. A decrease of shed CD31 levels measured at step (d) as compared to shed CD31 levels measured at step (b) indicates that the drug is effective for treating said patient.

More specifically, the invention relates to a method for monitoring the response of a patient suffering from a thrombotic or autoimmune disorder to a drug, said method comprising the steps of:
  a) detecting platelet-derived shed ectodomain, lymphocyte-derived shed ectodomain and/or soluble splice variant of CD31 in a biological sample of said patient before and after onset of a treatment of said patient with said drug;
  b) comparing the levels of said platelet-derived shed ectodomain, lymphocyte-derived shed ectodomain and/or soluble splice variant of CD31 detected at step (a); and, optionally,
  c) correlating a difference in said levels of platelet-derived shed ectodomain, lymphocyte-derived shed ectodomain and/or soluble splice variant of CD31 with the effectiveness of the drug for treating said patient.

In general, a decrease in the levels of platelet-derived shed ectodomain and/or lymphocyte-derived shed ectodomain of CD31 after onset of the treatment compared with the levels of said shed ectodomains of CD31 before onset of the treatment indicates that the patient responds to said drug, and that said drug is effective for treating said patient. Preferably, the decrease is of at least 5, 10, 25, 50, 75 or 90%. Conversely, if no significant difference in the levels of shed ectodomains of CD31 is found at step (b), or if an increase in the levels of shed ectodomains of CD31 after onset of the treatment is found at step (b), the patient does not respond to said drug and the drug is not effective for treating said patient.

Diagnostic Kits

The invention also contemplates diagnostic kit comprising:
a) optionally, at least one antibody which specifically binds to an epitope located in a region that is present on said lymphocyte-derived shed ectodomain, on platelet-derived shed ectodomains, and on said splice variant,
b) at least one antibody which specifically binds to an epitope located in a region that is present on said platelet-derived shed ectodomain and said splice variant, but absent from said lymphocyte-derived shed ectodomain;
c) at least one antibody which specifically binds to an epitope located in a region present in said splice variant, but absent from said platelet-derived shed ectodomain and said lymphocyte-derived shed ectodomain;

The antibodies may be linked to a support, such as a bead, as described above, and/or be detectably labeled as described above. Alternatively, the kit may further comprise a labeled detection ligand that binds to an epitope located in a region that is present on said lymphocyte-derived shed ectodomain, on platelet-derived shed ectodomains, and on said splice variant.

Said antibody (a) may be an antibody that specifically binds to an epitope located in a region that is present in the $1^{st}$, $2^{nd}$, $3^{rd}$, $4^{th}$ or $5^{th}$ extracellular immunoglobulin-like domains of CD31. Said antibody (b) may be an antibody that specifically binds to an epitope located in the $6^{th}$ extracellular immunoglobulin-like domain of CD31. Said third antibody (c) may be an antibody that specifically binds to an epitope located in a region that is present in the intracellular domain of said CD31. Suitable antibodies are described above.

Thus, the invention provides a diagnostic kit comprising:
a) a bead linked to an antibody that specifically binds to an epitope located in a region that is present in the $1^{st}$, $2^{nd}$, $3^{rd}$, $4^{th}$ or $5^{th}$ Ig-like extracellular domain of CD31;
b) a first labelled antibody that specifically binds to an epitope located in the $6^{th}$ extracellular immunoglobulin-like domain of CD31; and
c) a second labelled antibody that specifically binds to an epitope located in a region that is present in the $1^{st}$, $2^{nd}$, $3^{rd}$, $4^{th}$ or $5^{th}$ Ig-like like extracellular domain of CD31;
d) a third labelled antibody that specifically binds to an epitope located in a region that is present in the intracellular domain of said CD31.

Also provided is a diagnostic kit comprising:
a first type of bead linked to an antibody that specifically binds to an epitope located in the $6^{th}$ extracellular immunoglobulin-like domain of CD31;
a second type of bead linked to an antibody that specifically binds to an epitope located in a region that is present in the intracellular domain of said CD31; and optionally
a labelled antibody that specifically binds to an epitope located in a region that is present in the $1^{st}$, $2^{nd}$, $3^{rd}$, $4^{th}$ or $5^{th}$ extracellular immunoglobulin-like domains of CD31;

Also provided is a diagnostic kit comprising:
a bead linked to an antibody that specifically binds to an epitope located in a region that
a first type of labelled antibody that specifically binds to an epitope located in the $6^{th}$ extracellular immunoglobulin-like domain of CD31; and
a second type of labelled antibody that specifically binds to an epitope located in a region that is present in the $1^{st}$, $2^{nd}$, $3^{rd}$, $4^{th}$ or $5^{th}$ Ig-like extracellular domain of CD31.

Such kits can be used, e.g., in the diagnostic methods according to the invention, and/or in drug choice, and/or in drug monitoring.

Fluorescently labeled antibody may include fluorophores exited by a blue-laser and emitting in the FITC, PE, PerCP or PE-tandem channels, or excited by a red laser and emitting in the Cy5/APC or APC-tandem channels, or by a violet laser and emitting in the pacific blue or pacific orange channels or by a UV laser and emitting in the Quantum Dot channels);

These kits may additionally comprise other components such as e.g. reagents and/or instructions.

The kits may also comprise samples comprising a known amount of shed ectodomain of CD31 and/or of soluble splice variants, samples from healthy individuals and/or samples from individuals suffering from atherosclerosis or atherothrombosis.

The kits according to the invention may further comprise a fluorescently-labelled antibody that specifically binds to phosphoTyrosine or to phosphoSerine/Threonine.

The different antibodies used in the methods and kits for analyzing a molecular complex preferably do not cross-compete with each other.

Throughout the specification, terms such as 'comprises', 'comprised', 'comprising' and can have the meaning attributed to them in most patent jurisdictions, preferably in the jurisdiction in question; e.g. they can mean 'includes', 'included', 'including', etc. Terms such as 'consisting of' 'consisting essentially of' and 'consists essentially of' have the meaning ascribed to them in most patent jurisdictions, preferably in the jurisdiction in question; e.g., they may imply the exclusion of all, most, or all but a negligible amount of other elements, or they may allow for elements not explicitly recited, but exclude elements that are found in the prior art or that affect a basic or novel characteristic of the invention.

An 'isolated' peptide, protein or nucleic acid may be isolated substantially or completely away from one or more elements with which is associated in nature, such as other naturally occurring peptide, protein or nucleic acids or other peptide or nucleic acid sequences.

The term 'about' as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The invention will now be described in more detail by means of the following non-limiting figures and examples. All references cited herein, including journal articles or abstracts, published or unpublished patent application, issued patents or any other references, are hereby incorporated by reference in their entirety, including all data, tables, figures and text presented in the cited references.

DESCRIPTION OF THE FIGURES

Figure 2:
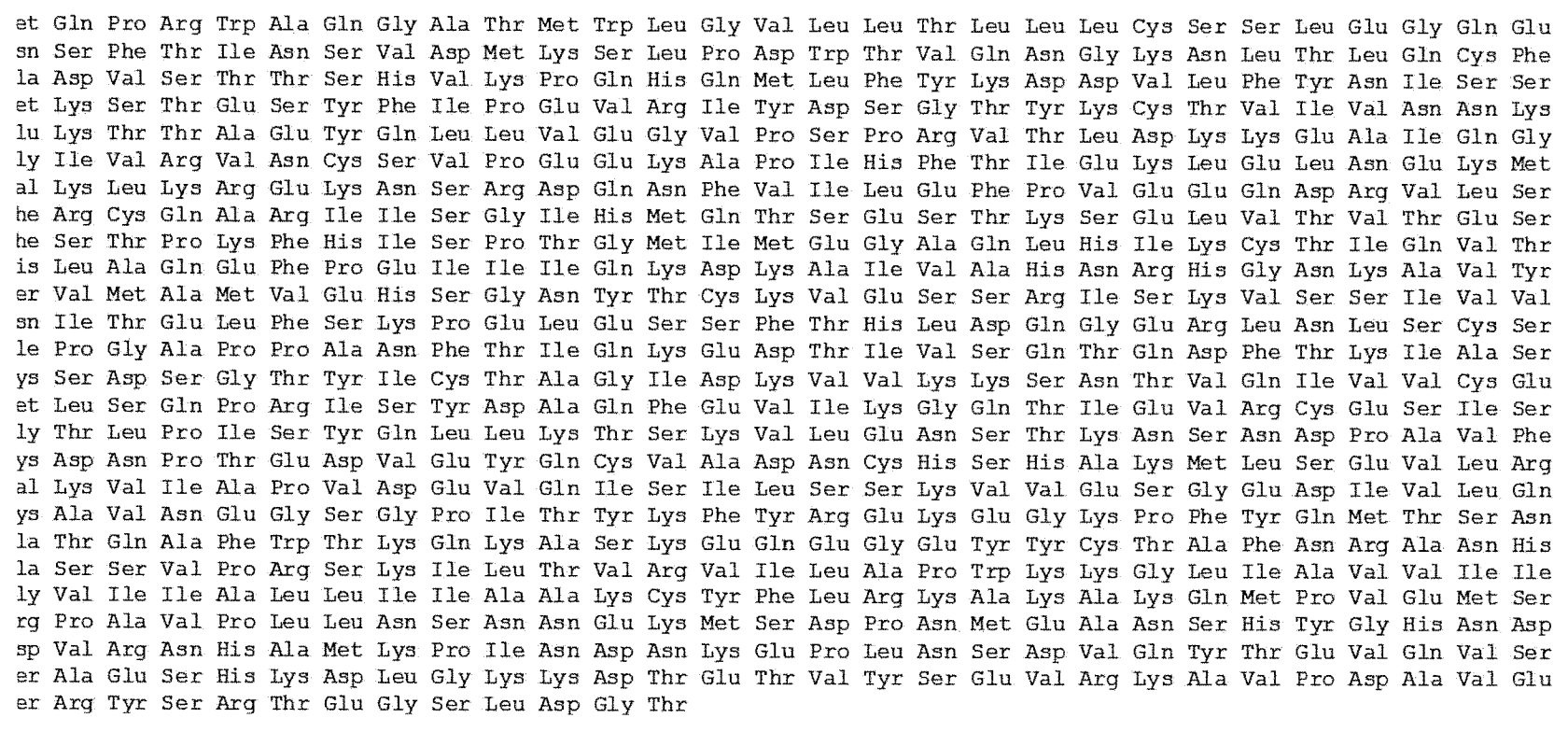

FIG. 2 shows the full-length amino acid sequence of human CD31.

EXAMPLES

Methods

Lymphocytes

Figure 1:
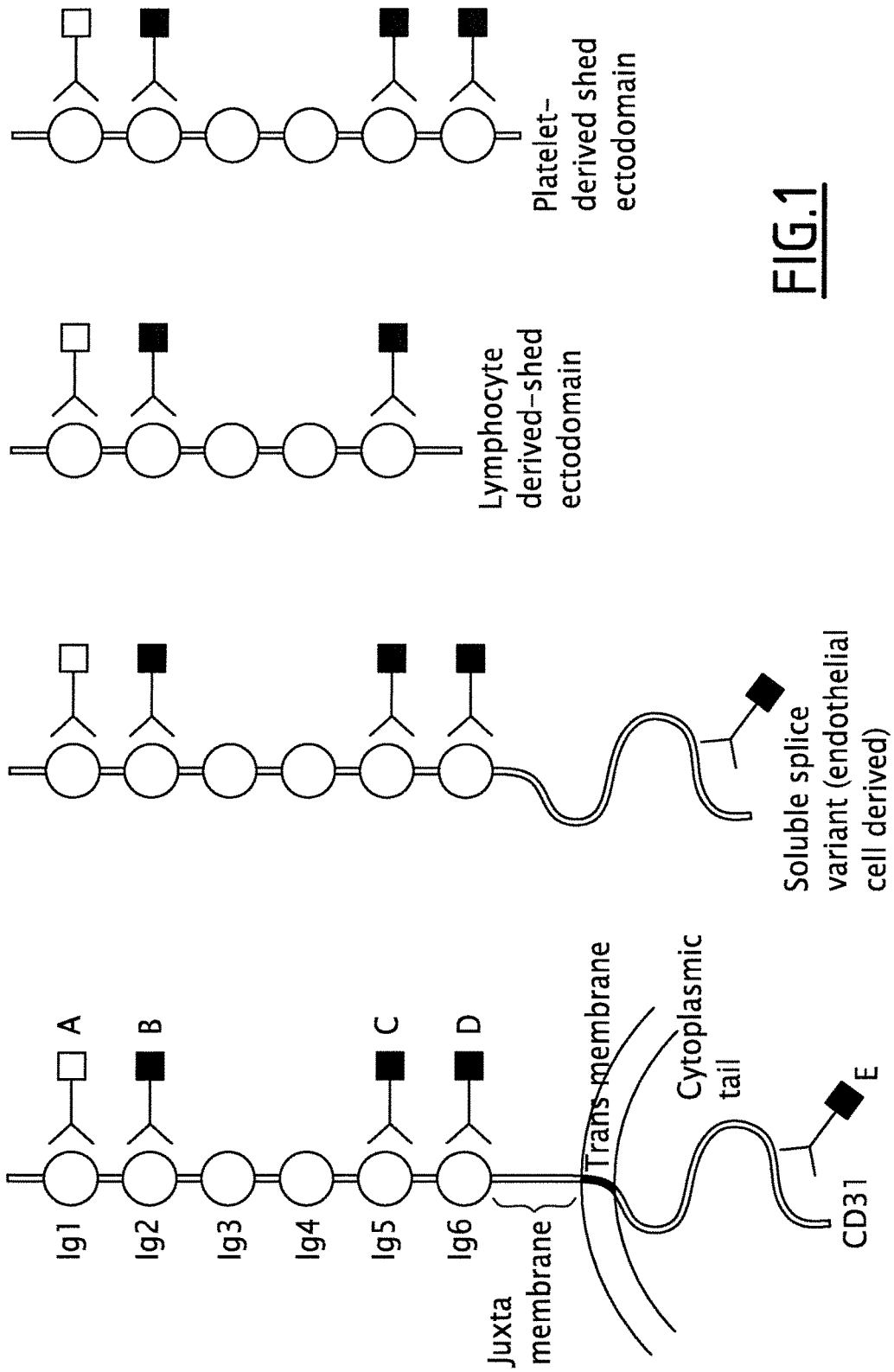
FIG. 1 is a schematic representation of the various forms of CD31, showing the full-length, membrane-anchored form including the transmembrane domain; the soluble splice variant lacking the transmembrane and juxtamembrane domains, the lymphocyte-derived shed ectodomain resulting from cleavage of the membrane-anchored form between the $5^{th}$ and $6^{th}$ extracellular domains and comprising extracellular domains 1 to 5; and the newly identified platelet-derived shed ectodomain resulting from cleavage of the membrane-anchored form between the $6^{th}$ Ig-like extracellular domain and the juxtamembrane domains and comprising extracellular domains 1 to 6.
Figure 3:
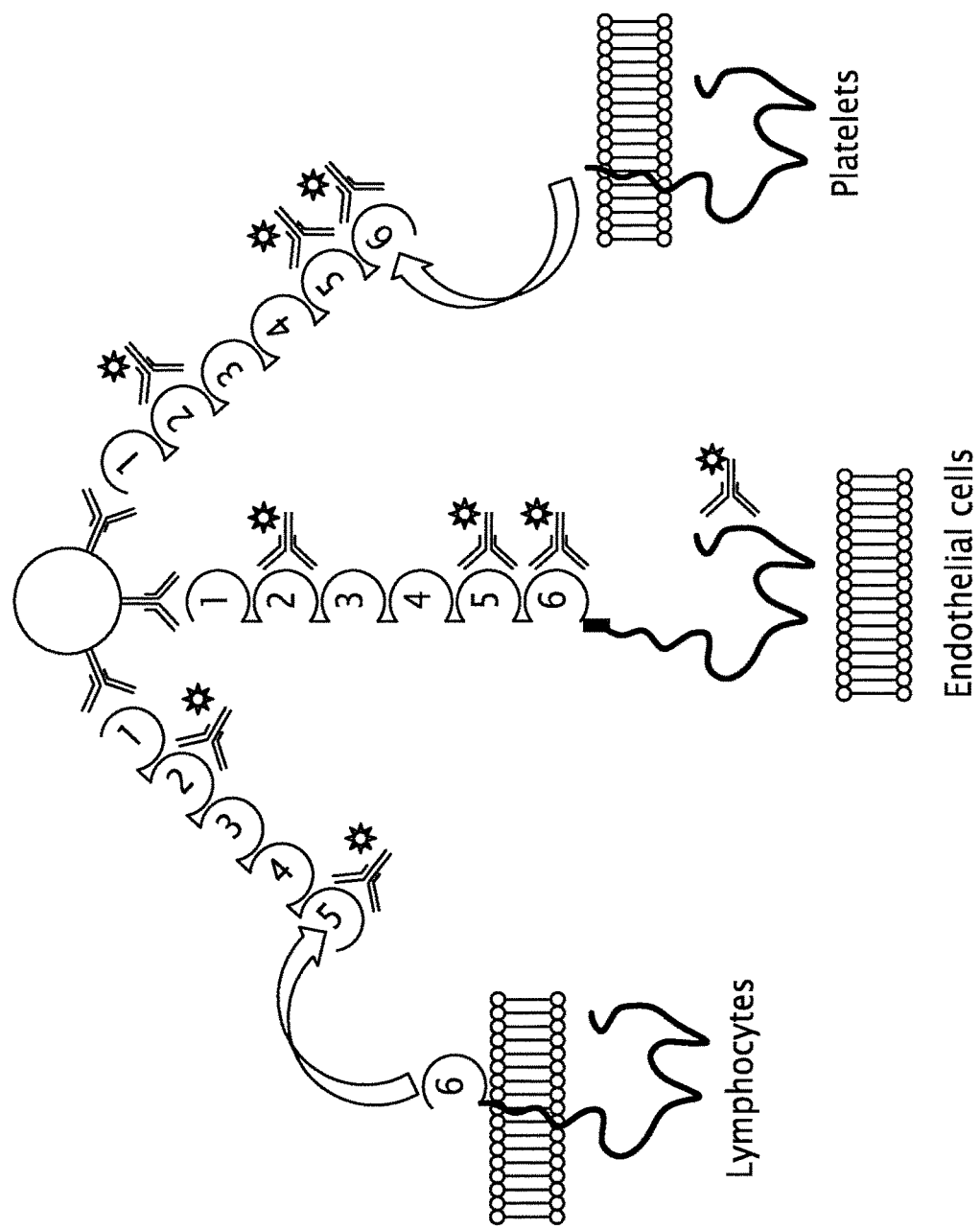
FIG. 3 represents an exemplary assay according to the invention. In this assay, beads carrying an antibody specific for the $1^{st}$ Ig-like extracellular domain of CD31 are used to pull down all soluble forms of CD31. The different forms of soluble CD31 may then be detected by using a labelled antibody which binds only the endothelial-cell-derived splice variant (antibody binding within the intracellular domain), a labelled antibody which binds to the splice variant and the platelet-derived shed ectodomain (antibody binding within the $6^{th}$ Ig-like domain), and labelled antibodies which binds to all 3 soluble forms (antibodies binding within the $2^{nd}$ and $5^{th}$ Ig-like domains).

Supernatants were prepared from activated T-lymphocytes and soluble CD31 detected as described in PCT/EP2009/058220 (WO2010/000756).

Ten-color flow cytometry was performed on peripheral blood leukocytes from 5 healthy individuals either in basal conditions or after overnight stimulation with soluble 1 µg/ml of purified anti-CD3 antibody (R&D Systems). Ten-color flow cytometry was performed after erythrocyte hypotonic lysis (10 minutes at 37° C. 1:10 v:v in Tris 10 mM, $NH_4Cl$ 155 mM, $KHCO_3$ 10 mM, pH 7.4) on heparinized peripheral blood leukocytes from 5 healthy individuals, fixed in PBS/Formaldehyde 1%/FCS 1% for 4 minutes at 37° C. prior to processing. Pelleted cells were incubated for 30 minutes at room temperature and protected from light with a cocktail of fluorescent monoclonal antibodies directed to CD3 (PE-Texas Red), CD4 (PE-Cy7), CD8 (PerCP), HLA-DR (APC-Cy7), CD45RA (Pacific Blue), and CD31 (WM59, PE) from BD Biosciences and anti-CD20 (AlexaFluor®700) and anti-CD31 (PECAM 1.2, FITC) from Invitrogen (1 µl of each). At least 50,000 events were acquired in the lymphocyte gate using a BD LSRII® equipped with 3 lasers (405, 488 and 633 nm) and analysed with BD DIVA® 6.0 software.

To detect the splice variant and lymphocyte-derived shed CD31 in plasma, a cytokine bead array (CBA®, BD) was used. Three differently functional CBA beads (A9, D5 and E9) were coupled with either one of the following purified monoclonal anti-CD31 antibodies JC70A (domain 1, DAKO), MEM-05 (domain 5, Zymed) and PECAM 1.2 (domain 6, Invitrogen). The coupled beads were then incubated with the culture supernatant and positive binding of circulating CD31 was detected by a fourth anti-CD31 monoclonal antibody, WM-59 (domains 1-2) coupled to PE (BD). The concentration of plasma CD31 including at least domain 1 (JC70A), or domains 1 to 5 (MEM-05) or all the extracellular domains 1 to 6 of CD31 (PECAM 1.2) was determined by analysing the median fluorescent intensity of the detecting antibody on ≥1000 gated beads on samples and serial dilutions of the same standard (recombinant, full length extracellular CD31, R&D Systems). The standard curve was obtained for each of the beads using the same known concentrations of the recombinant CD31 in order to overcome any bias due to differences in binding affinity of the diverse antibodies. The concentration in ng/ml of CD31 determined with PECAM 1.2 coupled beads (dom 1-6) was subtracted from the one obtained using MEM-05 coupled beads to obtain the amount of circulating CD31 lacking dom6 (dom 1-5). The latter was subtracted from the concentration of CD31 obtained using the JC70A-coupled beads to calculate the value of soluble CD31 lacking both dom 5 and 6 but containing at least domains 1 and 2 (dom 1-2).

Platelets

Platelets were prepared from fresh human blood obtained from healthy volunteers who had not ingested any drugs in the previous 10 days collected into acid-citrate-dextrose anticoagulant (ACDA, final concentration 13.6 mmol/L dextrose, pH 6.5). Platelet-rich plasma containing less that one leukocyte per $10^5$ platelets was collected by centrifugation at 800 g for 5 minutes at 20° C. Platelets were sedimented by centrifugation at 800 g for 11 minutes and washed in Hank's balanced salt solution (HBSS) modified by the addition of dextrose (4.45 mmol/L), $NaHCO3$ (3.35 mmol/L), $MgCl2$ (500 µmol/L) bovin serum albumin (fraction V, alcohol precipitated, 0.1%), pH 7.5 (with NaOH).

Platelet aggregation was monitored photometrically on a Chronolog (4 channels) agregometer at 37° C. Aliquots (240 µl) of suspended platelets in siliconized glass cuvettes containing stir bars were equilibrated at 37° C. for 5 minutes. $CaCl2$ (2.5 mmol/L final concentration) and collagen (horse collagen, final concentration 2.5 ng/L) were added 1 minute after the beginning of aggregation recording and supernatants were collected at 2, 5, 10 and 30 minutes following collagen-induced platelet aggregation.

Supernatants from aggregating platelets collected at the different times were centrifuged at 2500 g for 15 minutes in order to eliminate platelets and debris prior to detection.

CD31 detection in the platelet supernatant was carried out using pulldown with bead-conjugated antibodies to Ig like domain 5 (MEM-05, Exbio Praha) and detection with antibodies directed towards Ig-like domain 2 (WM59-PE, BD Biosciences) and Ig-like domain 6 (MBC78.2-Fitc, Caltag).

Figure 4:
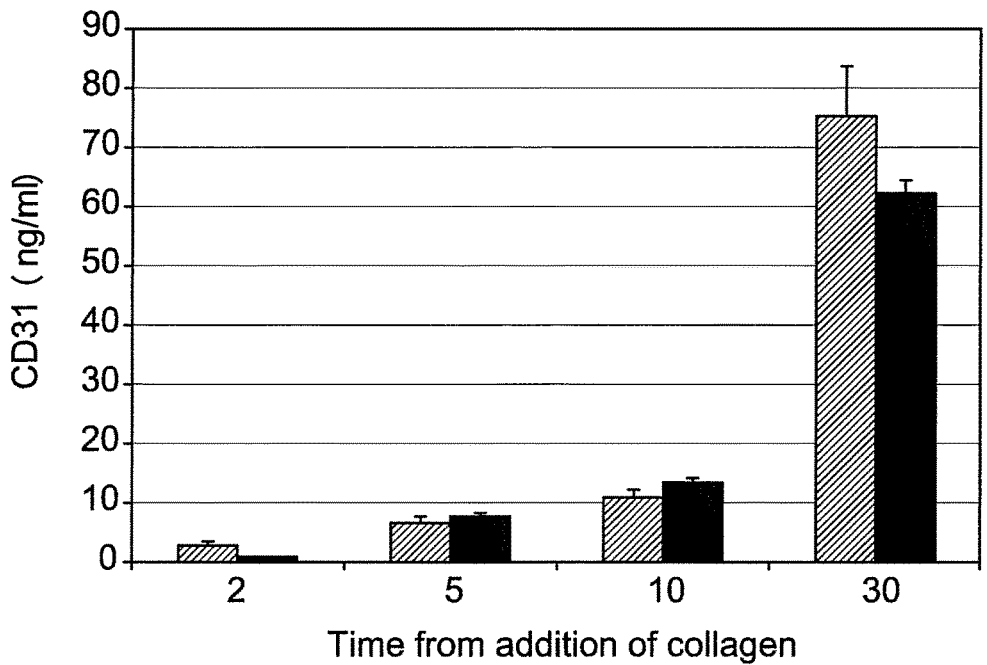
FIG. 4 shows CD31 detection in the supernatant of aggregating platelets using pulldown with antibodies to-Ig like domain 5 and detection with antibodies directed towards Ig-like domain 2 (grey) and Ig-like domain 6 (black).

Results:

As shown in FIG. 4, the CD31 fragment deriving from aggregating platelets and detectable in biological fluids contains both domain 5 and domain 6. This shows that platelets cleave the extracellular CD31 between the epitope of the antibody directed to domain 6 (MBC78.2) and the cell membrane.

Figure 5:
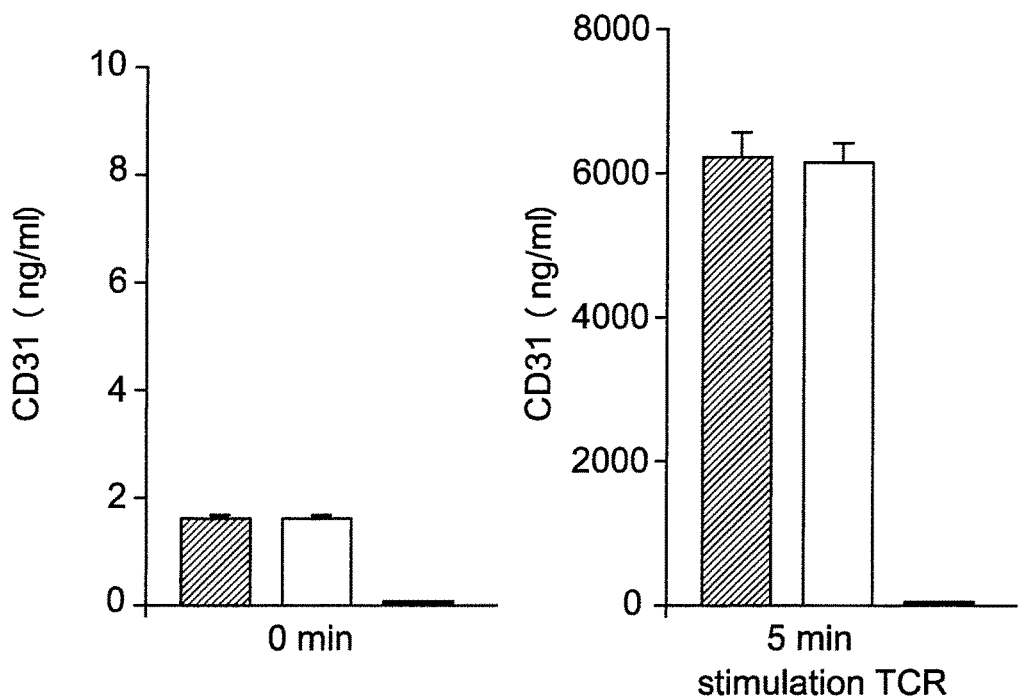
FIG. 5 shows CD31 detection in the supernatant of TCR (T cell receptor)-stimulated T lymphocytes using pulldown with antibodies to-Ig like domain 1 and detection with antibodies directed towards Ig-like domain 2 (grey), Ig-like domain 5 (white) and Ig-like domain 6 (black).

In contrast, as seen in FIG. 5, TCR(T cell receptor)-stimulated T-lymphocytes cleave their extracellular CD31 between domain 5 and domain 6. Thus, the CD31 cleaved by platelets can be distinguished from the one produced by T cells via the detection of domain 6 (positive in the case of platelets and negative in the case of T cell origin).

Simultaneous Detection of Platelet-Derived Shed Ectodomain, Lymphocyte-Derived Shed Ectodomain and Splice Variant CD31

Biological samples (e.g; plasma samples) are centrifuged at 2500 g for 15' in order to avoid biases due to freeze-thaw induced aggregates and microparticles. Fifty microliters of sample is incubated with functional cytometric (CBA or other) beads coupled to WM59 monoclonal purified antibodies (directed against human CD31 domain 1). Positive binding of soluble CD31 is detected by four other anti-CD31 monoclonal antibody, MBC78.3 (directed against human CD31 domain 2) coupled to FITC, MBC78.1 (directed against human CD31 domain 5) coupled to PE, MBC78.2 (directed against human CD31 domain 6) coupled to PerCp-Cy5.5).

Acquisition is performed with the DIVA 6.0 software on a LSRII cytometer equipped with a 96-well plate reader. The analysis is run with the FCAP Array® Software (BD Biosciences) and CD31 concentrations are obtained by the 4 parameter logistic formula. The standard curves are obtained with each of the detecting monoclonal fluorescent antibodies simultaneously used with the recombinant CD31 in order to overcome any bias due to differences in binding affinity of the diverse antibodies The concentration in pg/ml of total CD31 is determined by the green fluorescence (clone MBC78.3, CD31 domain 2). The endothelial-derived CD31 is determined with the median fluorescence of V450 (clone 235.1) because it is the only one that comprises the cytoplasmic tail. Platelet-shed CD31 is determined with the median fluorescence of PerCp-Cy5.5 (CD31 domain 6). This amount is subtracted from the one obtained with the median fluorescence of PE (CD31 domain 5) to yield the level of leukocyte-derived CD31. The subtraction of this fraction from the concentration of CD31 obtained with Fitc (CD31 domain 2) allows the quantification of smaller shed CD31 fractions that are negligible in healthy subjects but could be different in case of pathology.

The invention claimed is:

1. A method for detecting a platelet-derived shed ectodomain of a cluster of differentiation 31 (CD31) protein among soluble forms of CD31 in a biological sample, wherein said soluble forms include a soluble splice variant of said CD31 protein, wherein said platelet-derived shed ectodomain of a CD31 protein is a CD31 fragment (i) comprising the 1st to 5th extracellular immunoglobulin-like (Ig-like) domains and the whole or a part of the 6th extracellular Ig-like domain comprising an amino acid sequence corresponding to residues 494 to 501 of human CD31 protein and (ii) not comprising the intracellular domain of said full-length protein, the method comprising the steps of:

a) providing a first discriminating antibody, wherein the antibody specifically binds to an epitope located in a region that is present on said splice variant and on said platelet-derived shed ectodomain, wherein the antibody is labeled with a detectable label;

b) providing a second discriminating antibody, wherein the antibody specifically binds to an epitope located in a region that is present on said splice variant and absent from said platelet-derived shed ectodomain, wherein the antibody is labeled with a detectable label;

c) contacting said antibodies with the biological sample;

d) measuring the signal obtained from each detectable label;

wherein said first discriminating antibody binds to the 6th Ig-like extracellular domain of said CD31;

and wherein said second discriminating antibody binds to the intracellular domain of said CD31.

2. The method according to claim 1, further comprising the step of calculating the percentage and/or the amount of said soluble forms that corresponds to said platelet-derived shed ectodomain, and/or the step of calculating either the ratio of platelet-derived shed ectodomain to soluble forms, or the ratio of soluble splice variant to soluble forms.

3. The method of claim 1, wherein said method comprises a step of providing a capture antibody before step a), wherein said capture antibody specifically binds to an epitope located in a region that is present both on said a platelet-derived shed ectodomain and on said splice variant.

4. The method of claim 3, wherein said capture antibody is immobilized on a solid support.

5. The method of claim 3, wherein said capture antibody binds to a region within the $1^{st}$, $2^{nd}$, $3^{rd}$, $4^{th}$, $5^{th}$ or $6^{th}$ Ig-like extracellular domain of said CD31.

6. The method according to claim 1, wherein the signal in step c) is measured by flow cytometry.

7. The method according to claim 1, wherein said biological sample is plasma, blood or urine.

8. The method according to claim 1, wherein said biological sample is obtained from an individual suffering from or at risk of suffering from a thrombotic or an autoimmune disorder.

9. The method of claim 1, wherein said first discriminating antibody is selected from the group consisting of the antibodies MBC78.2, PECAM1.1, PECAM 1.2 and HC1/6.

10. The method of claim 1, wherein said second discriminating antibody is selected from the group consisting of the antibodies MBC235.1 and SP38.

11. The method of claim 3, wherein said capture antibody is selected from the group consisting of PECAM 1.1, PECAM 1.2, HC1/6, MBC78.2, MEM-05, MBC78.1, JC70A, 9G11, WM59 and MBC78.3.

12. A method for detecting a platelet-derived shed ectodomain of a cluster of differentiation 31 (CD31) protein among soluble forms of CD31 in a biological sample, wherein said soluble forms include a soluble splice variant of said CD31 protein, wherein said platelet-derived shed ectodomain of a CD31 protein is a CD31 fragment (i) comprising the $1^{st}$ to $5^{th}$ extracellular immunoglobulin-like (Ig-like) domains and the whole or a part of the $6^{th}$ extracellular Ig-like domain comprising an amino acid sequence corresponding to residues 494 to 501 of human CD31 protein and (ii) not comprising the intracellular domain of said full-length protein, the method comprising the steps of:

a) providing a first discriminating antibody, wherein the antibody specifically binds to an epitope located in a region that is present on said splice variant and on said platelet-derived shed ectodomain, wherein the antibody is labeled with a detectable label;

b) providing a second discriminating antibody, wherein the antibody specifically binds to an epitope located in a region that is present on said splice variant and absent from said platelet-derived shed ectodomain, wherein the antibody is labeled with a detectable label;

c) contacting said antibodies with the biological sample;

d) measuring the signal obtained from each detectable label;

wherein said first discriminating antibody binds to the $6^{th}$ Ig-like extracellular domain of said CD31 and wherein said first discriminating antibody is selected from the group consisting of the antibodies MBC78.2, PECAM1.1, PECAM 1.2, HC1/6 and antibodies binding to the same epitope;

and wherein said second discriminating antibody binds to the intracellular domain of said CD31, and wherein said second discriminating antibody is selected from the group consisting of the antibodies MBC235.1, SP38 and antibodies binding to the same epitope.

13. The method of claim 12, wherein said method comprises a step of providing a capture antibody before step a), wherein said capture antibody specifically binds to an epitope located in a region that is present both on said platelet-derived shed ectodomain and on said splice variant and wherein said capture antibody is selected from the group consisting of PECAM 1.1, PECAM 1.2, HC1/6, MBC78.2, MEM-05, MBC78.1, JC70A, 9G11, WM59, MBC78.3 and antibodies binding to the same epitope.

14. A method of detection of platelet aggregation in a subject, said method comprising the detection of a CD31 protein fragment wherein said fragment is a platelet-derived shed ectodomain of a CD31 protein comprising (i) the whole or a part of the 6th extracellular Ig-like domain of said full-length CD31 protein comprising an amino acid sequence corresponding to residues 494 to 501 of human CD31 protein and (ii) not comprising the intracellular domain of said full-length CD31 protein in a biological sample from a subject, wherein the step of detecting said CD31 protein fragment is performed according to the method as defined in claim 1.

15. A method of diagnosis of thrombosis said method comprising the detection of a CD31 protein fragment wherein said fragment is a platelet-derived shed ectodomain of a CD31 protein comprising (i) the whole or a part of the 6th extracellular Ig-like domain comprising an amino acid sequence corresponding to residues 494 to 501 of human CD31 protein and (ii) not comprising the intracellular domain of said full-length CD31 protein in a biological sample from a subject, wherein the step of detecting said CD31 protein fragment is performed according to the method as defined in claim 1.

* * * * *